(12) United States Patent
Bruehwiler et al.

(10) Patent No.: US 9,717,860 B2
(45) Date of Patent: Aug. 1, 2017

(54) NEEDLE CHANGING APPARATUS

(71) Applicant: Becton, Dickinson and Company, Franklin Lakes, NJ (US)

(72) Inventors: Michel Bruehwiler, Newton, MA (US); Cole Constantineau, Cambridge, MA (US); Ryan Schoonmaker, Oceanside, CA (US); James Bates, Sparta, NJ (US); Robert Banik, Edgewater, NJ (US); Margaret Taylor, Groton, MA (US)

( * ) Notice: Subject to any disclaimer, the term of this patent is extended or adjusted under 35 U.S.C. 154(b) by 0 days.

(21) Appl. No.: 15/250,423

(22) Filed: Aug. 29, 2016

(65) Prior Publication Data

US 2016/0361487 A1    Dec. 15, 2016

Related U.S. Application Data

(63) Continuation of application No. 13/206,438, filed on Aug. 9, 2011, now Pat. No. 9,427,514.
(Continued)

(51) Int. Cl.
*A61M 5/32* (2006.01)
*A61M 5/00* (2006.01)
*A61B 5/15* (2006.01)
*A61M 5/31* (2006.01)

(52) U.S. Cl.
CPC ..... *A61M 5/3205* (2013.01); *A61B 5/150389* (2013.01); *A61M 5/002* (2013.01);
(Continued)

(58) Field of Classification Search
CPC ............ A61M 2005/004; A61M 5/002; A61M 5/3205; A61M 5/3243; A61M 3/00; A61M 5/00; A61M 5/178; A61M 5/31; A61M 5/32; A61M 5/3206; A61M 5/3208; A61M 5/321; A61M 5/322; A61M 5/3232; A61M 5/3245
(Continued)

(56) References Cited

U.S. PATENT DOCUMENTS 5,971,966 A    10/1999   Lav
6,616,616 B2   9/2003    Fritz et al.
(Continued)

FOREIGN PATENT DOCUMENTS

JP    2007-531591 A    11/2007
JP    2008-520339 A    6/2008
(Continued)

*Primary Examiner* — Jason Flick
(74) *Attorney, Agent, or Firm* — Dickinson Wright PLLC

(57) ABSTRACT

An apparatus is disclosed for storing and changing needles for connection with a medicament delivery device, comprising an inner housing, a reservoir disposed within the inner housing, and a needle holder disposed within the inner housing, for fluidly connecting a medicament container of the medicament delivery device with the reservoir. The apparatus also includes a plurality of patient needles displaceably disposed on the needle holder, and an outer housing displaceably disposed about the inner housing and providing a user interface to individually select one of the plurality of patient needles, connect the selected needle with the reservoir, expose the selected needle outside of the apparatus for injection, and store the selected needle.

6 Claims, 38 Drawing Sheets

Related U.S. Application Data

(60) Provisional application No. 61/344,525, filed on Aug. 16, 2010.

(52) U.S. Cl.
CPC ........ *A61M 5/3243* (2013.01); *A61M 5/3298* (2013.01); *A61M 2005/004* (2013.01); *A61M 2005/312* (2013.01)

(58) Field of Classification Search
USPC ........................................................ 604/192
See application file for complete search history.

(56) References Cited

U.S. PATENT DOCUMENTS

| | | |
|---|---|---|
| 6,783,537 B1 | 8/2004 | Kuhr et al. |
| 7,544,185 B2 | 6/2009 | Bengtsson |
| 2002/0020646 A1 | 2/2002 | Groth et al. |
| 2008/0312604 A1 | 12/2008 | Boesen |
| 2009/0227958 A1 | 9/2009 | Burroughs et al. |
| 2010/0152660 A1 | 6/2010 | Mack et al. |
| 2012/0016315 A1* | 1/2012 | Radmer ................ A61M 5/008 604/240 |

FOREIGN PATENT DOCUMENTS

| | | |
|---|---|---|
| WO | WO-0200101 | 1/2002 |
| WO | WO-2004004812 A1 | 1/2004 |
| WO | WO-2004107975 A2 | 12/2004 |
| WO | WO-2005097237 A1 | 10/2005 |
| WO | WO-2008150715 A1 | 12/2008 |
| WO | WO-2009016161 A1 | 2/2009 |
| WO | WO-2010044064 A1 | 4/2010 |
| WO | WO-2011083055 A1 | 7/2011 |

* cited by examiner

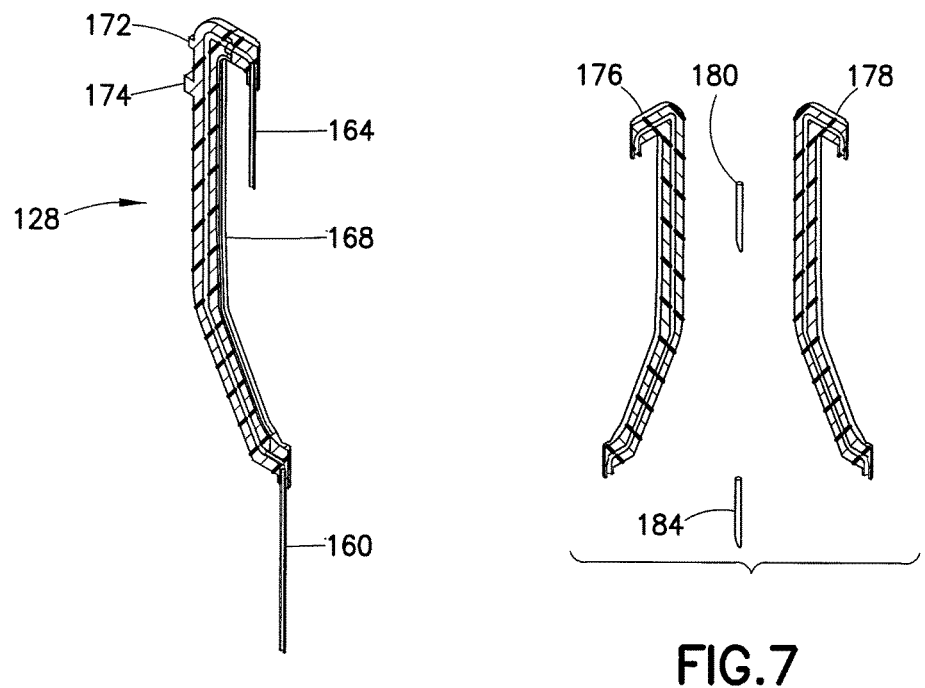
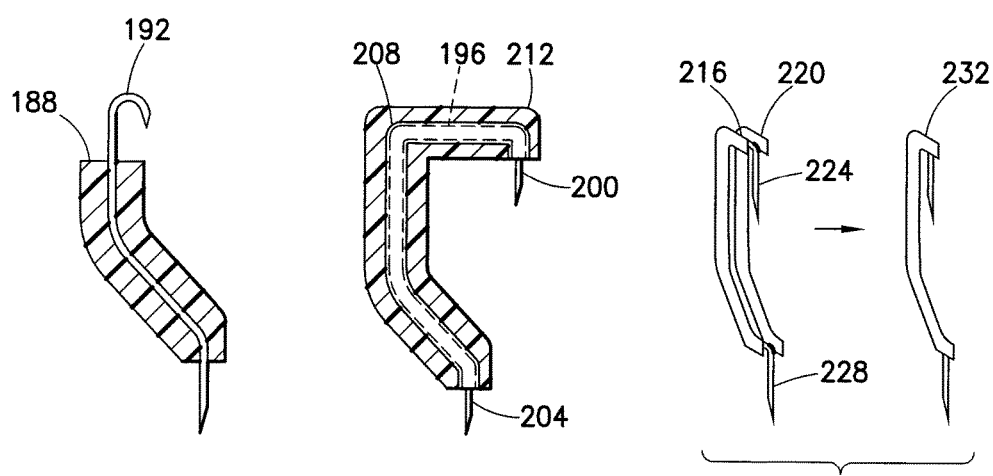
FIG.6  FIG.7  FIG.8  FIG.9  FIG.10

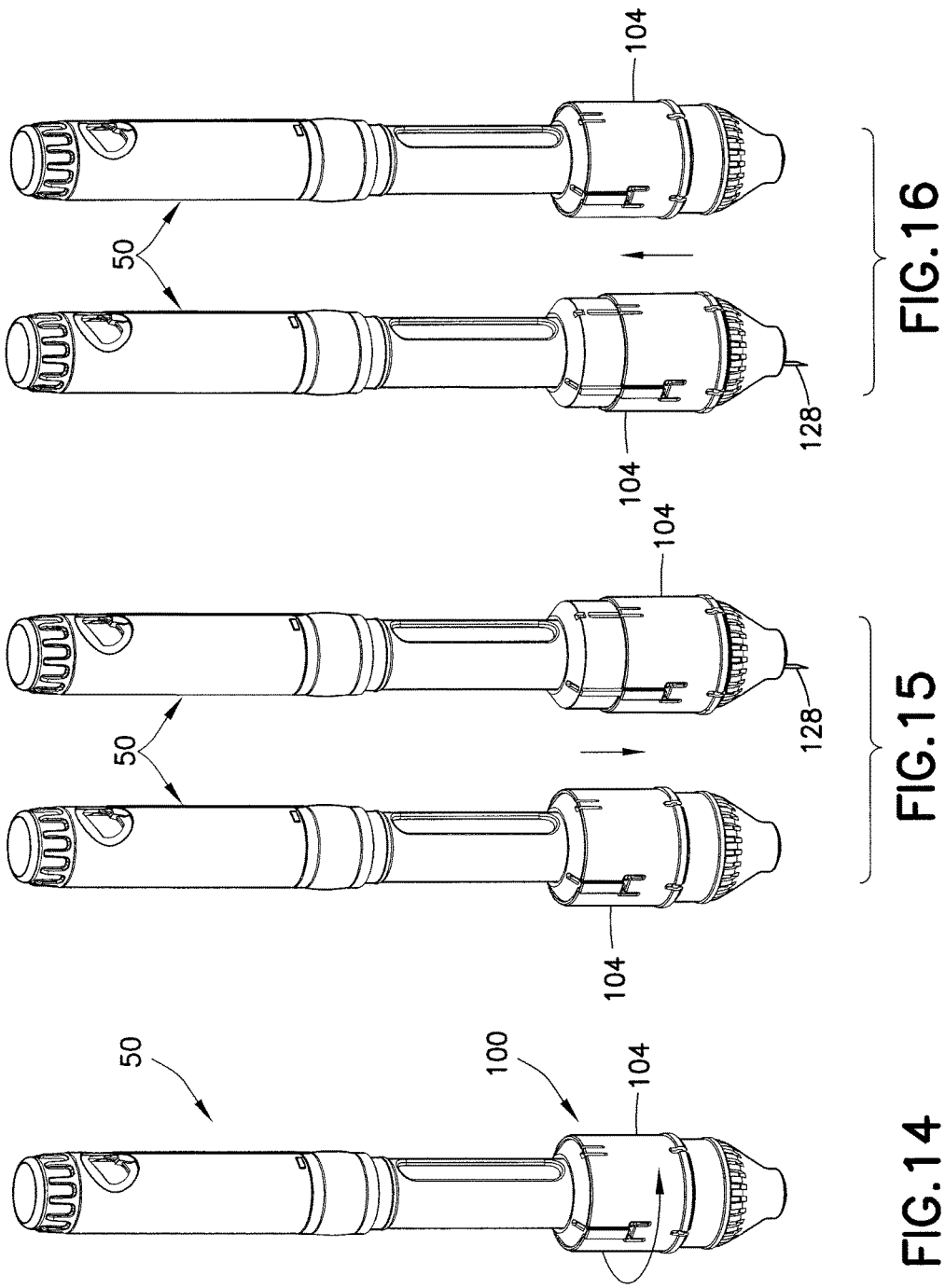

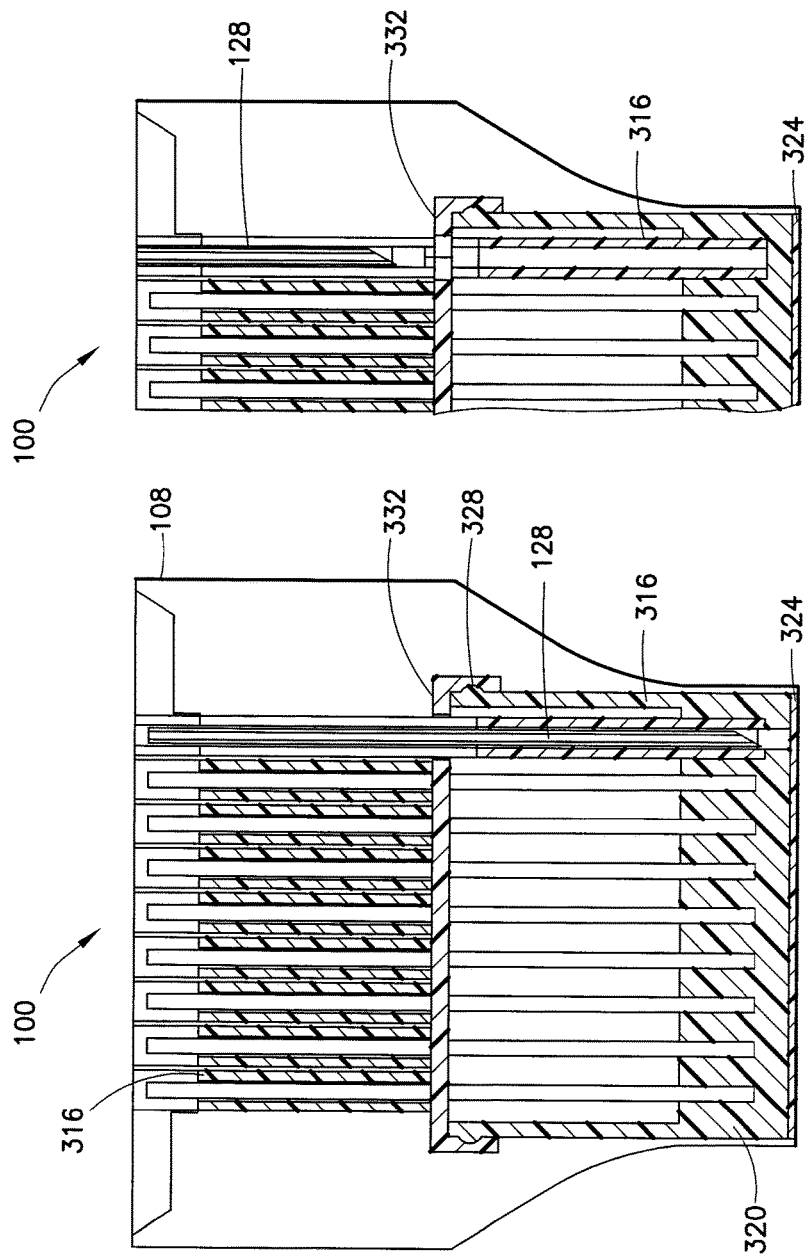

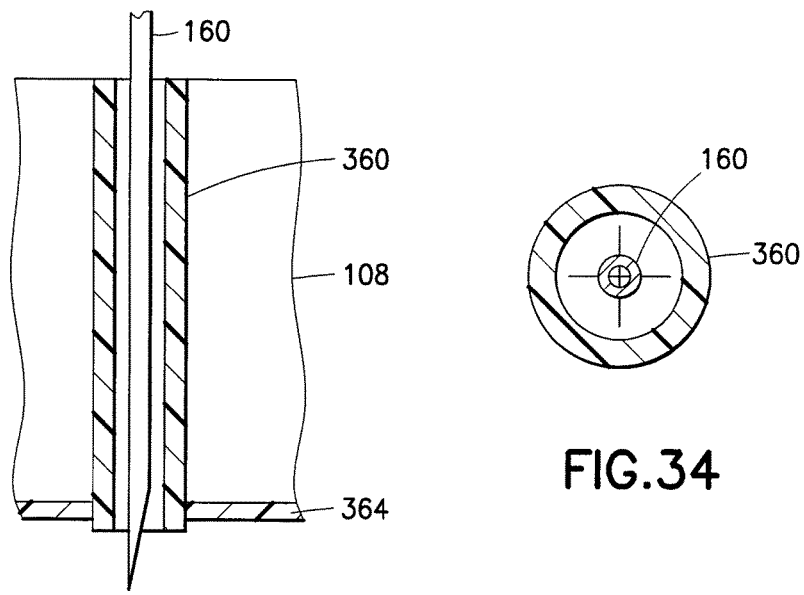
FIG.33
FIG.34
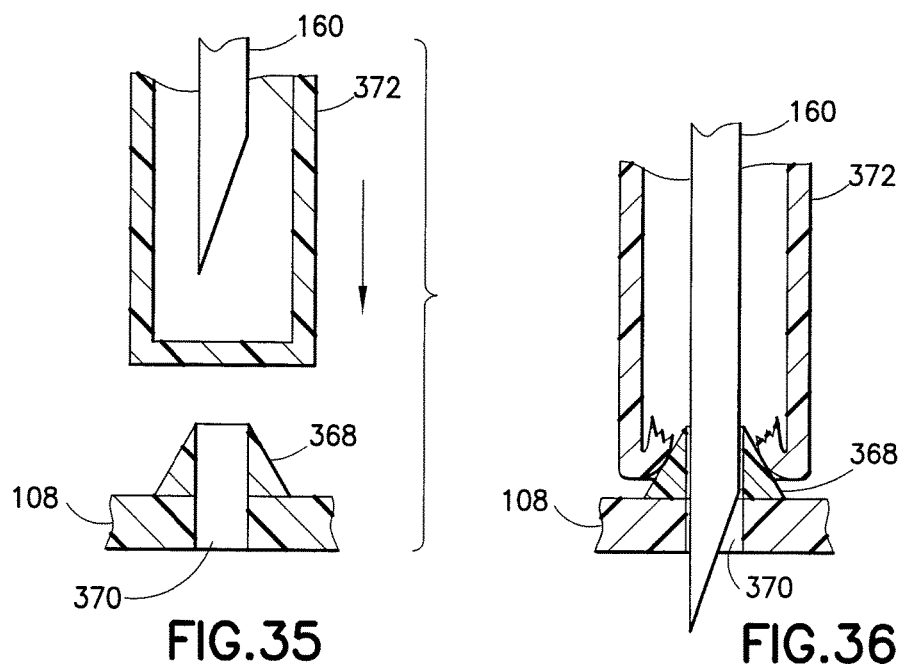
FIG.35
FIG.36

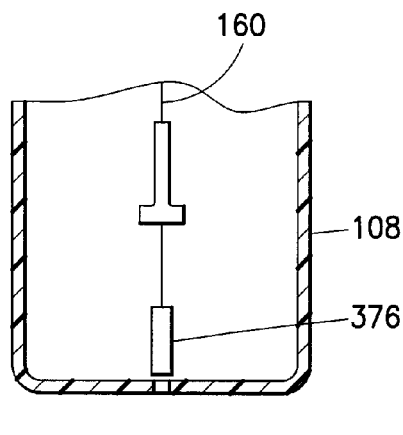
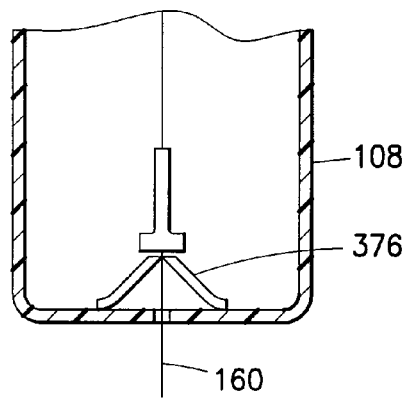
FIG.41    FIG.42
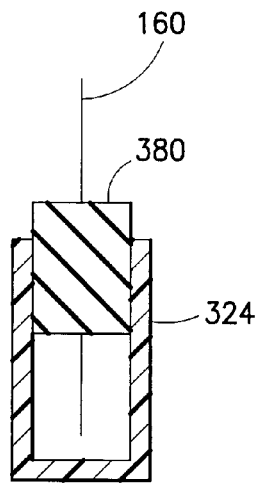
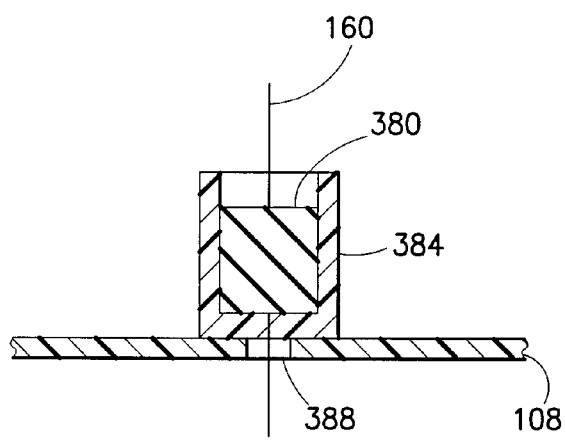
FIG.43    FIG.44

NEEDLE CHANGING APPARATUS

CROSS-REFERENCE TO RELATED APPLICATIONS

This application is a continuation of U.S. patent application Ser. No. 13/206,438, filed on Aug. 9, 2011, which claims priority under 35 USC §119(e) from U.S. Provisional Patent Application Ser. No. 61/344,525, filed on Aug. 16, 2010, the disclosure of both of said prior applications being incorporated herein by reference in their entirety.

BACKGROUND OF THE INVENTION

1. Field of the Invention

The present invention relates to needles for a medicament delivery device, such as a pen injection device or a syringe, and more particularly, to a multiple needle changing apparatus for a medicament delivery device.

2. Description of the Related Art

Medicament delivery devices are used for self-injection of precisely measured doses of medication. Pen injection devices are widely used, for example, by diabetics to self-inject insulin. A typical medicament delivery pen includes a cartridge that contains a volume of liquid medication sufficient for several doses. Using a pen needle attached to the pen injection device, the dose is injected into a tissue area, such as the intramuscular tissue layer, the subcutaneous tissue layer, or the intradermal tissue layer.

The assembly and operation of a typical pen injection device is described in commonly-assigned U.S. Patent Application Publication No. 2006/0229562, published on Oct. 12, 2006, which is hereby incorporated by reference in its entirety.

Pen injection devices, such as an exemplary pen injector 50 shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is employed by the user to securely hold the pen injector 50 in a shirt pocket, purse, or other suitable location.

FIG. 2 is an exploded view of the exemplary drug delivery pen 50 shown in FIG. 1. The dose knob/button 24 has a dual purpose and is used to both set the dosage of the medication to be injected and to inject the dosed medicament via a lead screw 7 and stopper 15 from a medicament cartridge 12, which is attached to the drug delivery pen through a lower housing 17. The medicament cartridge 12 is typically a glass tube sealed at one end with a septum 16 and at the other end with the stopper 15. In standard drug delivery pens, the dosing and delivery mechanisms are all found within the outer sleeve 13. Those mechanisms are not described in greater detail herein as they are understood by those knowledgeable of the art.

A pen needle assembly 10 includes a hub 20, a patient needle 11 extending from a patient end of the pen needle assembly, and a septum-penetrating needle cannula 18 disposed within the hub 20 on a non-patient side thereof. The septum-penetrating needle cannula 18 is in fluid communication with the patient needle 11. The hub 20 is preferably screwed onto the lower housing 17, although other attachment means can be used such as attaching directly to the medicament cartridge 12. In attaching the hub 20 to the lower housing 17 or medicament cartridge 12, the septum-penetrating cannula 18 pierces the septum 16, but the septum 16 does not move with respect to the medicament cartridge 12. The stopper 15, however, is axially displaceable within the medicament cartridge 12 while maintaining a fluid-tight seal. The distal movement of the plunger or stopper 15 within the medicament cartridge 12 (due to advancement of the lead screw 7) causes medication to be forced into the patient needle 11 of the hub 20.

To protect a user, or anyone who handles the pen injector 50, an outer shield 29, which attaches to the hub 20, covers the hub 20. The outer shield 29 can also be used as a handle or grip to screw hub 20 onto or off of pen injector 50. An inner shield 28 covers the patient needle 11 within the outer shield 29. The inner shield 28 can be secured to the hub 20 to cover the patient needle 11 by any suitable means, such as an interference fit or a snap fit. As shown in FIG. 2, the hub 20 also includes ribs 64 for engaging the outer shield 29. The outer shield 29 and inner shield 28 are removed prior to use. The cap 21 fits snugly against outer sleeve 13 to allow a user to securely carry the pen injection device 50.

To use the pen needle assembly 10, the user removes a sterile cover on the outer shield 29, twists the pen needle assembly 10 onto the pen injector 50, removes the outer shield 29, and then finally removes the inner shield 28. While there are some needle storage devices that aid in placing the pen needle assembly 10 on the pen injector 50, the user still must remove needle hub packaging, including the inner and outer shields 28 and 29, to place a needle hub onto a pen injector and ready the device for injection. This process must be repeated for each successive injection.

Pen needle assemblies are usually sold individually packaged inside a plastic cover (such as outer shield 29) with a label covering the opening in the cover to provide a sterility barrier. A need exists for a needle dispensing and storing apparatus that stores a plurality of needles before and after their use.

SUMMARY OF EMBODIMENTS OF THE INVENTION

It is an aspect of the present invention to provide an apparatus for changing needles. It is also an aspect of the present invention to provide an apparatus for storing needles prior to their use as well as subsequent to their use. Additionally, it is an aspect of the present invention to provide an apparatus for changing needles for connection with a medicament delivery device.

The foregoing and/or other aspects of the present invention are achieved by providing an apparatus for storing and changing needles for connection with a medicament delivery device, including an inner housing, a reservoir disposed within the inner housing, and a needle holder disposed within the inner housing, for fluidly connecting a medicament container of the medicament delivery device with the reservoir. The apparatus also includes a plurality of patient needles displaceably disposed on the needle holder, and an outer housing displaceably disposed about the inner housing and providing a user interface to individually select one of the plurality of patient needles, connect the selected needle with the reservoir, expose the selected needle outside of the apparatus for injection, and store the selected needle.

The foregoing and/or other aspects of the present invention are also achieved by providing a method of selecting a needle for a medicament delivery device having a medicament container, including the operations of connecting the medicament delivery device to an apparatus for storing and changing needles, establishing fluid communication between the medicament container and a reservoir within an inner housing of the apparatus, and rotating an outer housing of the apparatus relative to the inner housing to select one of a plurality of needles movably disposed on a needle holder, which is disposed within the inner housing. The method also includes the operations of axially displacing the outer housing relative to the inner housing in a distal direction away from the medicament delivery device, thereby fluidly connecting a selected one of the plurality of needles with the reservoir and exposing a patient end of the selected needle outside of the apparatus, and axially displacing the outer housing in a proximal direction to re-sheath the selected needle within the inner housing.

The foregoing and/or other aspects of the present invention are also achieved by providing an apparatus for storing and changing needles for connection with a medicament delivery device, including an inner housing, a reservoir disposed within the inner housing, and a needle holder disposed within the inner housing, for fluidly connecting a medicament container of the medicament delivery device with the reservoir. The apparatus also includes a plurality of patient needles displaceably disposed on the needle holder, and an outer housing rotatable relative to the inner housing for selecting one of the plurality of patient needles, and axially displaceable relative to the inner housing for connecting the selected needle with the reservoir, exposing the selected needle outside of the apparatus for injection, and re-sheathing the selected needle within the inner housing.

Additional and/or other aspects and advantages of the present invention will be set forth in part in the description that follows and, in part, will be apparent from the description, or may be learned by practice of the invention.

BRIEF DESCRIPTION OF THE DRAWINGS

The above and/or other aspects and advantages of embodiments of the invention will become apparent and more readily appreciated from the following detailed description, taken in conjunction with the accompanying drawings, in which:

FIG. 6 is a perspective view of a needle of the needle changing device of FIG. 3;

FIGS. 7-11 are perspective views illustrating alternative embodiments of needles of the needle changing device of FIG. 3;

FIGS. 14-16 are perspective views of the coupled pen injector of FIG. 1 and the needle changing device of FIG. 3 illustrating an overview of the operation thereof;

FIGS. 30 and 31 are perspective views in cross-section of a first alternative sterility barrier for the needle changing device of FIG. 3;

FIG. 33 is a perspective view in cross-section and FIG. 34 is a perspective view, together illustrating a third alternative sterility barrier for the needle changing device of FIG. 3;

FIGS. 35 and 36 are perspective views in cross-section of a fourth alternative sterility barrier for the needle changing device of FIG. 3;

FIGS. 39-42 are perspective views in cross-section of a fifth alternative sterility barrier for the needle changing device of FIG. 3;

FIGS. 43 and 44 are perspective views in cross-section of a sixth alternative sterility barrier for the needle changing device of FIG. 3;

FIG. 60 is a final needle for use with the needle changing device of FIG. 3 or the needle changing device of FIG. 53.

DETAILED DESCRIPTION OF EMBODIMENTS OF THE PRESENT INVENTION

Figure 1:
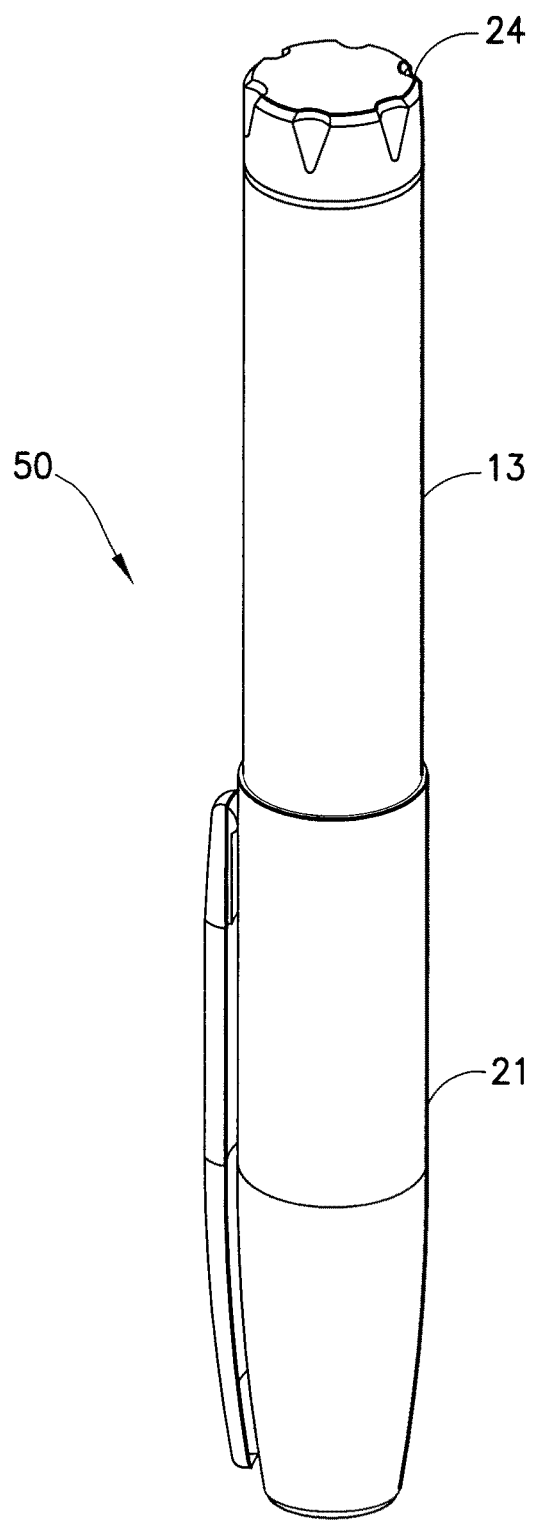
FIG. 1 is a perspective view of an exemplary drug delivery pen.
Figure 2:
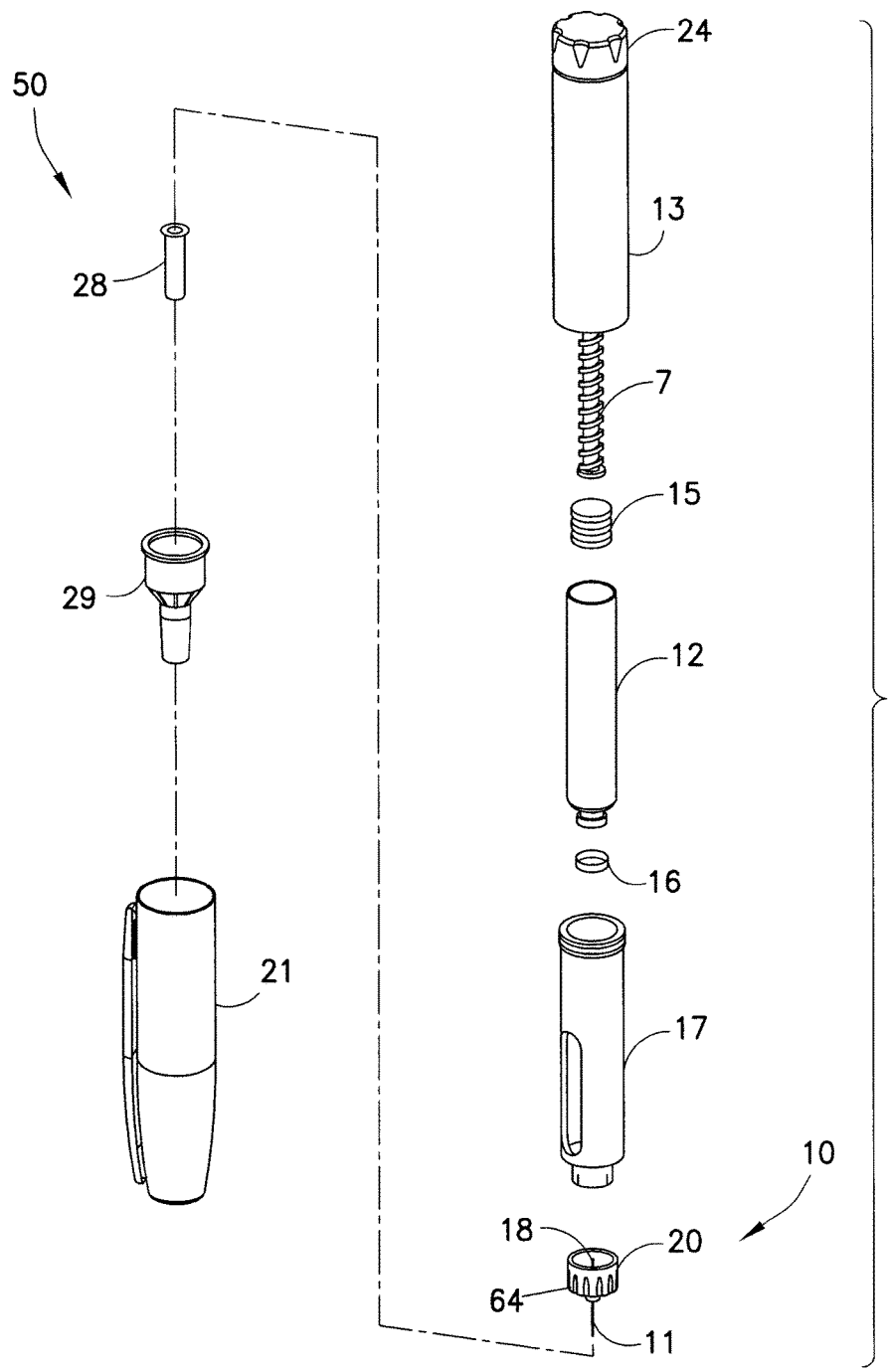
FIG. 2 is an exploded view of the exemplary drug delivery pen of FIG. 1.

Reference will now be made in detail to embodiments of the present invention, examples of which are illustrated in the accompanying drawings, wherein like reference numerals refer to the like elements throughout. The embodiments described herein exemplify, but do not limit, the present invention by referring to the drawings. As will be understood by one skilled in the art, terms such as up, down, bottom, and top are relative, and are employed to aid illustration, but are not limiting.

Figure 3:
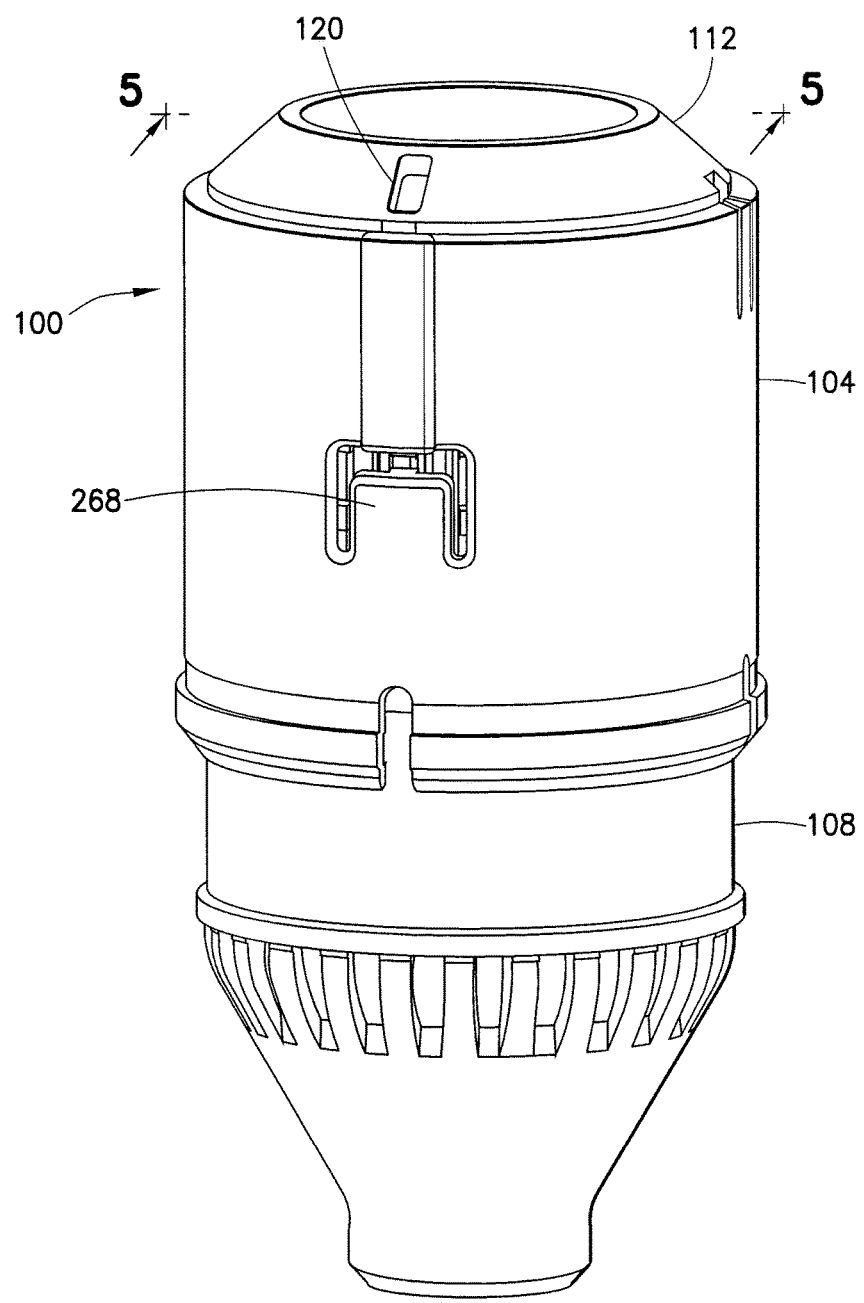
FIG. 3 is a perspective view of a needle changing device in accordance with an embodiment of the present invention.

FIG. 3 is a perspective view of a needle changing device 100 adapted to be connected to a pen injector (not shown) in accordance with an embodiment of the present invention. For brevity, the phrase "changing device 100" will be used hereinafter instead of "needle changing device 100." As shown in FIG. 3, the changing device 100 includes an outer housing 104, an inner housing 108, and a counter ring retainer 112. The outer housing 104 provides a user interface and is movably disposed with respect to the inner housing 108. The counter ring retainer 112 retains a needle counter or counter ring 116 (described in greater detail below) and has a window 120 disposed therein for viewing the number of remaining unused needles in the changing device 100.

Figure 4:
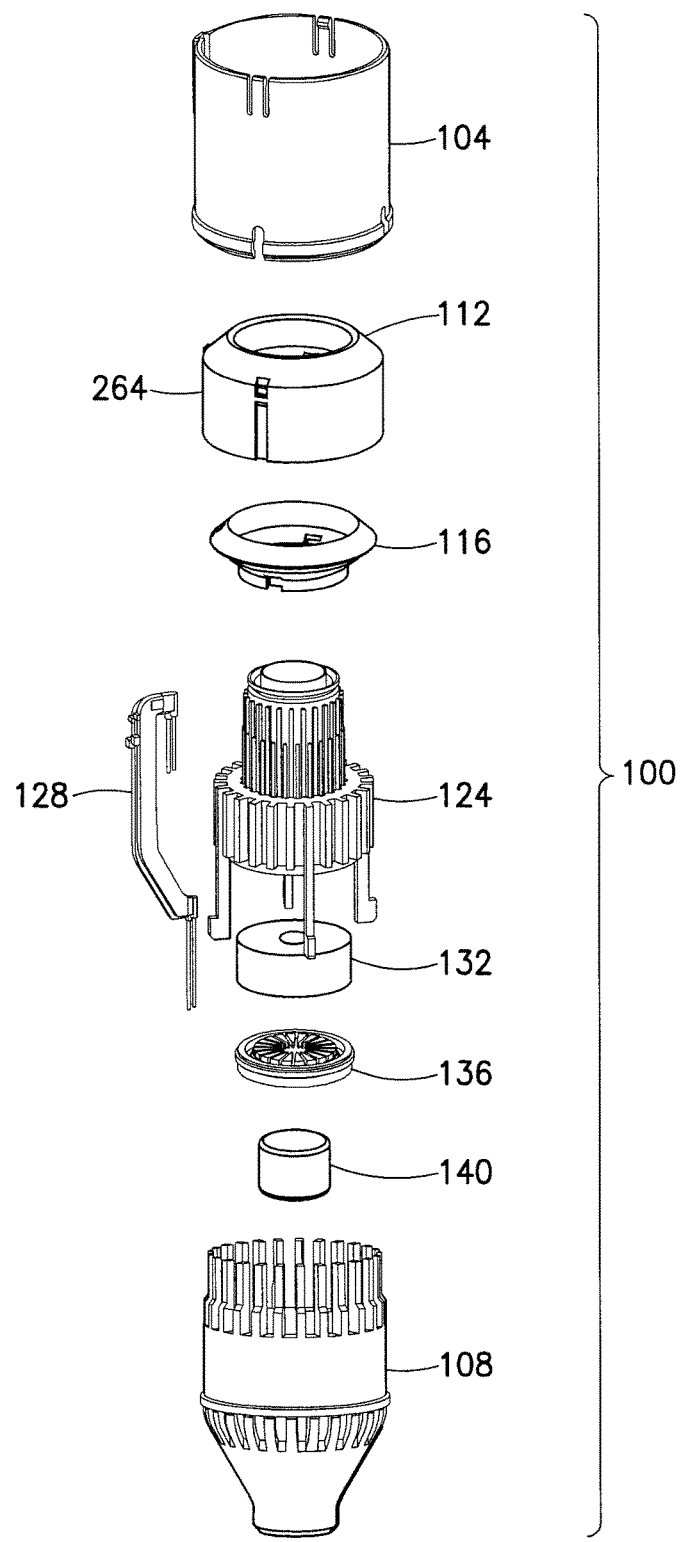
FIG. 4 is an exploded perspective view of the needle changing device of FIG. 3.

FIG. 4 is an exploded perspective view of the changing device 100. In addition to the outer housing 104, the inner housing 108, and the counter ring retainer 112, as shown in FIG. 4, the changing device 100 also includes a needle counter 116 the needle holder 124 plurality of needles 128 (though only a single needle 128 as shown in FIG. 4 for clarity), a self-sealing annular reservoir septum 132, a reservoir plate 136, and a self-sealing patient end septum 140. The reservoir plate 136 has a recess therein that, in conjunction with the reservoir septum 132, forms a reservoir 148.

Though not shown in FIG. 4, and described in greater detail below, the needle holder 124 also includes a lumen member or septum penetrating needle cannula 144 (visible in FIG. 5) for connecting the reservoir 148 with a medicament cartridge of a pen injector, such as the medicament cartridge 12 of the pen injector 50. Though one of ordinary skill in the art will understand that other pen injectors may be used, for brevity, hereinafter, the pen injector 50 will be used as an exemplary pen injector.

A method for assembling the changing device 100 includes the operations of inserting the reservoir septum 132 into a bottom of the needle holder 124, and inserting the reservoir plate into the needle holder 124 and onto the reservoir septum 132 to form the reservoir 148. The method also includes the operations of inserting a plurality of needles 128 onto the needle holder 124, inserting the patient ends of the plurality of needles 128 into the patient end septum 140, inserting the counter ring 116 and the counter ring retainer 112 onto a top of the needle holder 124, inserting the needle holder 124 into the inner housing 108 such that the patient end septum 140 is disposed at a patient ends thereof, and inserting the inner housing 108 and the counter ring retainer 112 within the outer housing 104.

Figure 5:
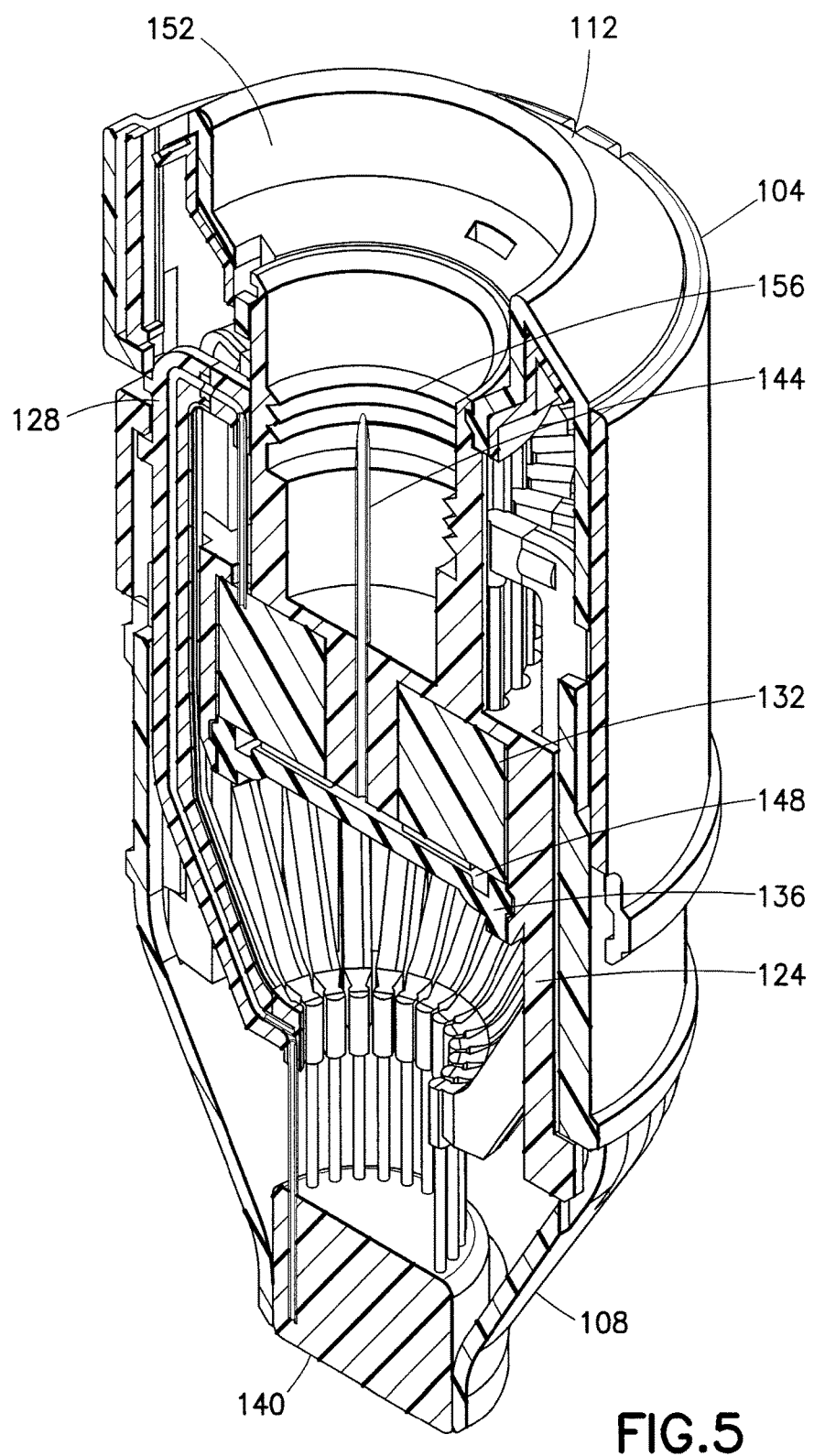
FIG. 5 is a perspective view in cross-section taken along line 5-5 in FIG. 3 of the needle changing device of FIG. 3.

FIG. 5 is a perspective view in cross-section taken along line 5-5 in FIG. 3 of the changing device 100. FIG. 5 illustrates a plurality of needles 128 arrayed circumferentially around the outside of the needle holder 124. As shown in FIG. 5, the reservoir plate 136, in conjunction with the reservoir septum 132 forms the reservoir 148. A non-patient end of the changing device 100 includes a space 152 for connecting the pen injector 50 to the changing device 100 for example, by employing threading 156 to screw the pen injector 50 into the changing device 100. Additionally, the septum penetrating needle cannula 144 fluidly connects the reservoir 148 with space 152. When the pen injector 50 is connected to the changing device 100, the septum penetrating needle cannula 144 fluidly connects the reservoir 148 with the medicament cartridge 12.

Further, as shown in FIG. 5, the patient end septum 140 is disposed at a patient end of the changing device 100. During storage, both before and after use, the patient ends of the respective needles 128 are disposed within the patient end septum 140. Thus, the patient end septum 148 provides a sterility barrier for the needles 128. Similarly, both before and after use, the non-patient end of the respective needles 128 are disposed within the reservoir septum 132, thereby providing a sterility barrier.

As shown in FIG. 6, the ear-shaped needle 128 includes a patient portion 160, a septum penetrating portion 164, and a connecting portion 168 fluidly connecting the septum penetrating portion 164 and the patient portion 160. Both the patient portion 160 and the septum penetrating portion 164 point in substantially the same direction. In other words, the patient portion 160 and the septum penetrating portion 164 are substantially parallel to each other, and are oriented in substantially the same direction. Put another way, the patient portion 160 and the septum penetrating portion 164 both point toward the patient end of the changing device 100.

Referring back to FIG. 5, because of the above-described needle geometry, the reservoir septum 132 is reversed with respect to the direction of a typical cartridge septum. Thus, the septum penetrating portion 164 penetrates the reservoir septum 132 from above. As shown in FIG. 6 and as described in greater detail below, an exterior side (with respect to the needle holder 124) of the connecting portion 168 has upper and lower needle protrusions 172 and 174 disposed thereon.

According to one embodiment, both the patient portion 160 and the penetrating portion 164 are formed of metal, for example, steel or stainless steel. Alternatively, the patient portion 160 and the penetrating portion can be formed of plastic. Additionally, according to one embodiment, the connecting portion 168 is formed of plastic, for example, polypropylene (PP) or polyethylene (PE). Further, according to one embodiment, the connecting portion 168 is integrally formed as a single unit by suspending patient portion 160 and the penetrating portion 164 in the connecting portion 168, for example, by a medical-grade adhesive.

FIGS. 7-10 are perspective views illustrating alternative embodiments of needles of the changing device 100. In FIG. 7, two opposing side pieces 176 and 178 are sealed together capturing a septum needle 180 and a patient needle 184. The septum needle 180, because it does not interface with the patient, can be formed of metal or, alternatively, of plastic. Further, in an alternative embodiment (not shown), a plastic septum needle 180 can be integrated into either of the two opposing side pieces 176 and 178, or mating halves of a plastic septum needle 180 can be disposed on the side pieces 176 and 178. The side pieces 176 and 178 each have the recessed channels therein. When the side pieces 176 and 178 are sealed together (for example, by a medical-grade adhesive, or heat, or radiation) the recesses form a fluid path between the septum needle 180 and the patient needle 184.

FIG. 8 illustrates an embodiment in which a needle receptacle 188 is over-molded onto a bent needle 192. As shown in FIG. 9, a tube 196 providing a fluid pathway between a septum needle 200 and a patient needle 204 clips into a recess 208 of a needle receptacle 212. The two needles are bonded to the tube 196 or, alternatively, to the receptacle 212. In FIG. 10, thin halves 216 and 220 are bonded over a septum needle 224 and a patient needle 228 establishing a fluid path therebetween, and producing needle 232.

Figure 11:
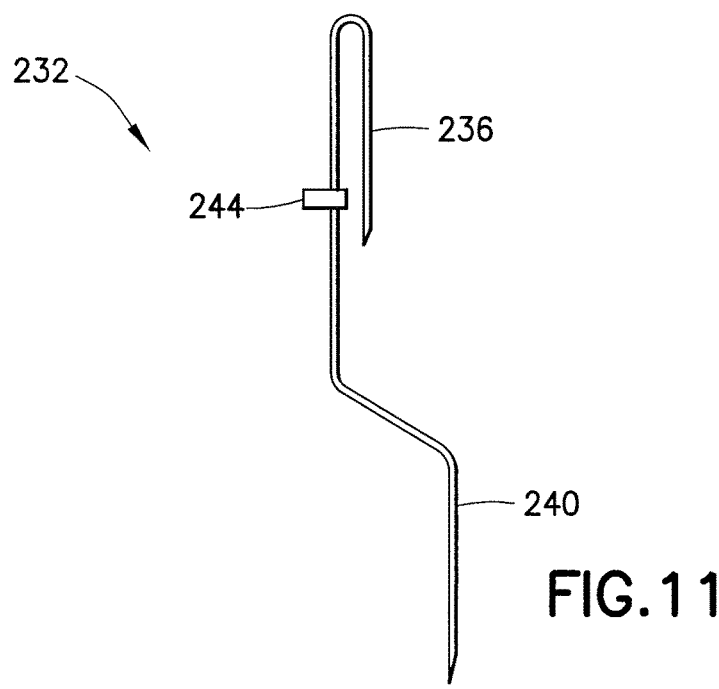
Figure 12:
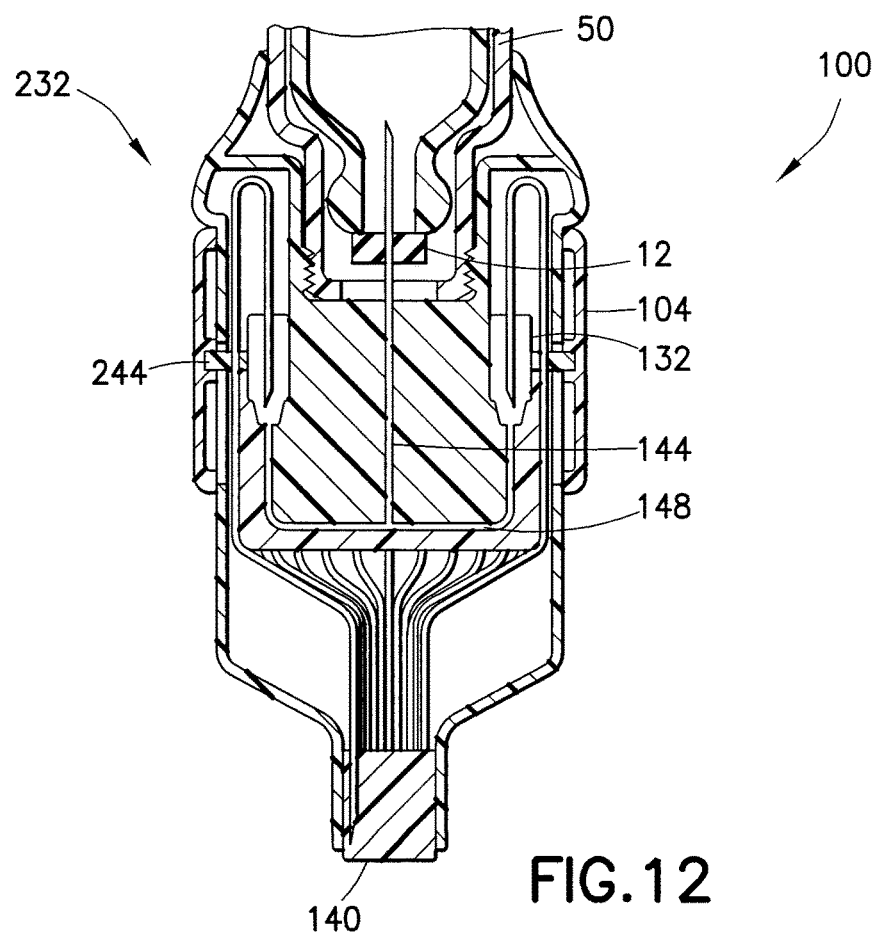
FIG. 12 is a perspective view in cross-section of a needle changing device in accordance with an embodiment of the present invention employing the needle of FIG. 11.

FIG. 11 is a perspective view of another alternative embodiment of a needle for the changing device 100. As shown in FIG. 11, the needle 232 is a single needle with a septum end 236 and a patient end 240. The septum end 236 is for piercing the reservoir septum 132, thereby fluidly connecting the reservoir 148 and the patient end 240. The needle 232 also includes a needle receptacle 244 for moving the needle 232 relative to the reservoir 240. FIG. 12 is a perspective view in cross-section of a needle changing device in accordance with an embodiment of the present invention employing the needle of FIG. 11. FIG. 12 illustrates a state of the changing device 100 prior to deployment of the needle 232. As shown in FIG. 12, the septum end 236 of the needle 232 penetrates the reservoir septum 132 and the patient end 240 penetrates the patient end septum 140. Additionally, the outer housing 104 is engaged with the needle receptacle 244 and thus, as will be described in greater detail below, the needle 232 is ready for deployment.

Figure 13:
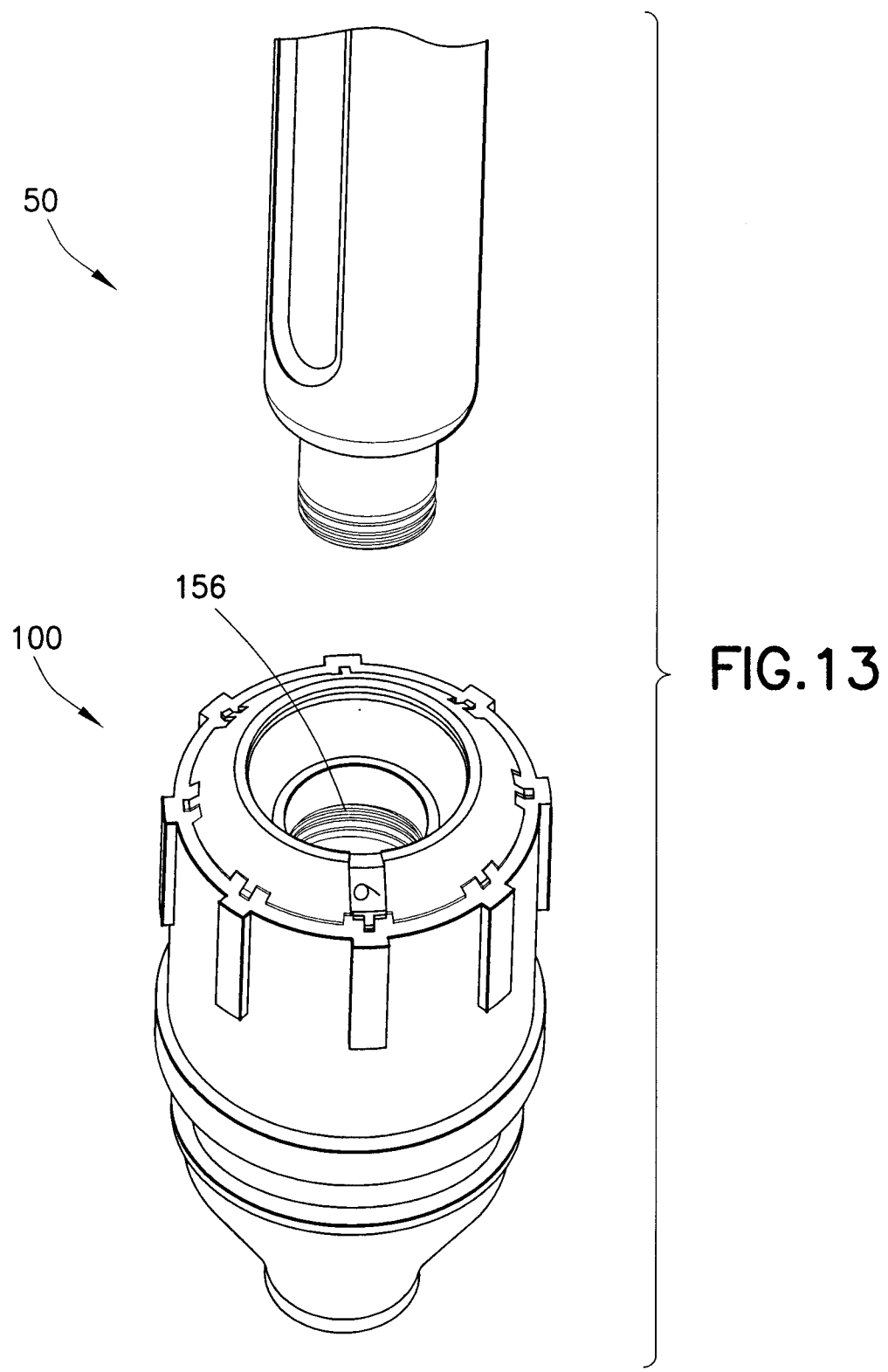
FIG. 13 is a perspective view of the pen injector of FIG. 1 and the needle changing device of FIG. 3 prior to the coupling thereof.

FIG. 13 is a perspective view of the pen injector 50 and the changing device 100 prior to the coupling thereof. To connect the pen injector 50 with the changing device 100, according to one embodiment, the user threads the pen injector 50 into the changing device 100 using, for example, screw threads 156.

FIGS. 14-16 are perspective views of the coupled pen injector 50 and the changing device 100 illustrating an overview of the operation thereof. As shown in FIG. 14, the user first rotates the outer housing 104 to select an unused needle, for example needle 128 or needle 232. Subsequently, as shown in FIG. 15 the user moves the outer housing 104 axially away from the pen injector 50, thereby exposing needle 128. In other words, the user slides the outer housing 104 down, or distally with respect to the pen injector 50 to expose the needle 128. After dispensing the medicament, as shown in FIG. 16, the user moves the outer housing 104 toward the pen injector 50, thereby re-sheathing the needle 128. Put another way, the user slides the outer housing 104 up, or proximally with respect to the pen injector 50 to withdraw the needle 128, thereby effectively and safely storing the used needle 128.

Figure 17:
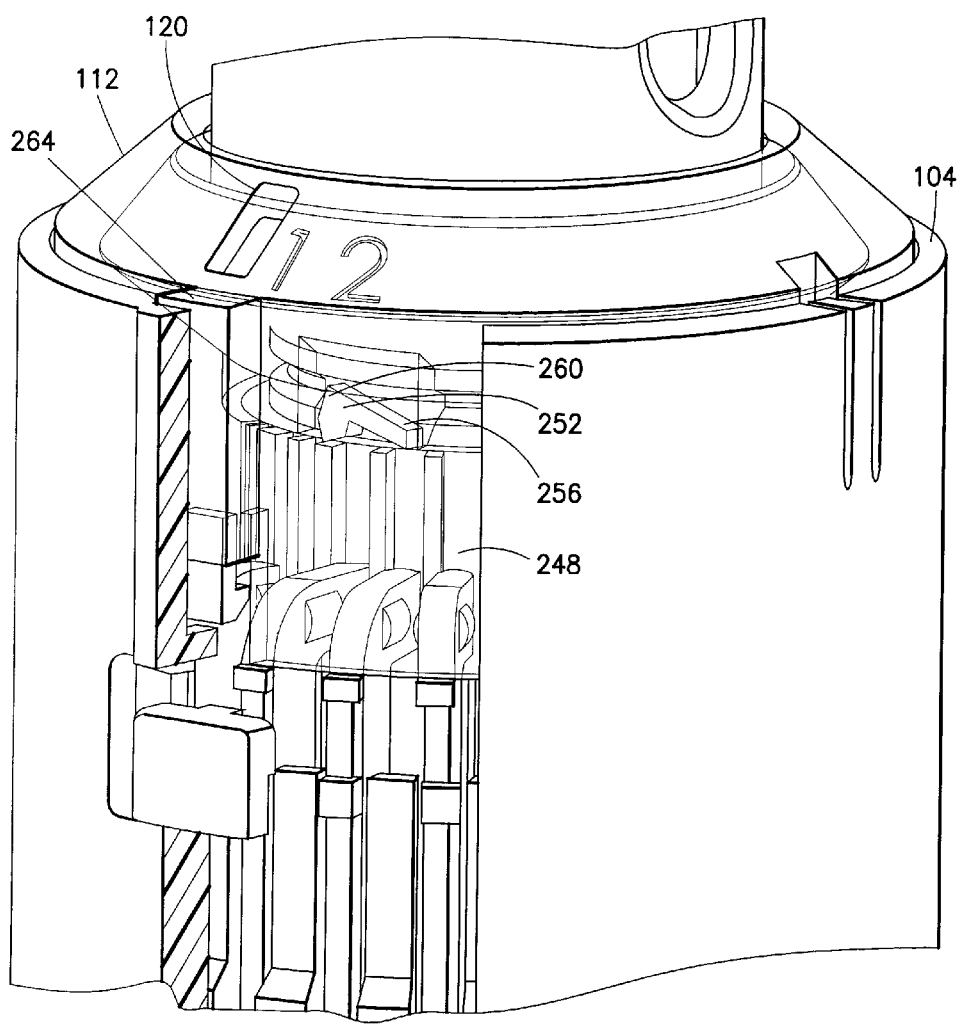
FIGS. 17-29 are perspective partial cutaway views illustrating the operation of the needle changing device of FIG. 3 in more detail.
Figure 18:
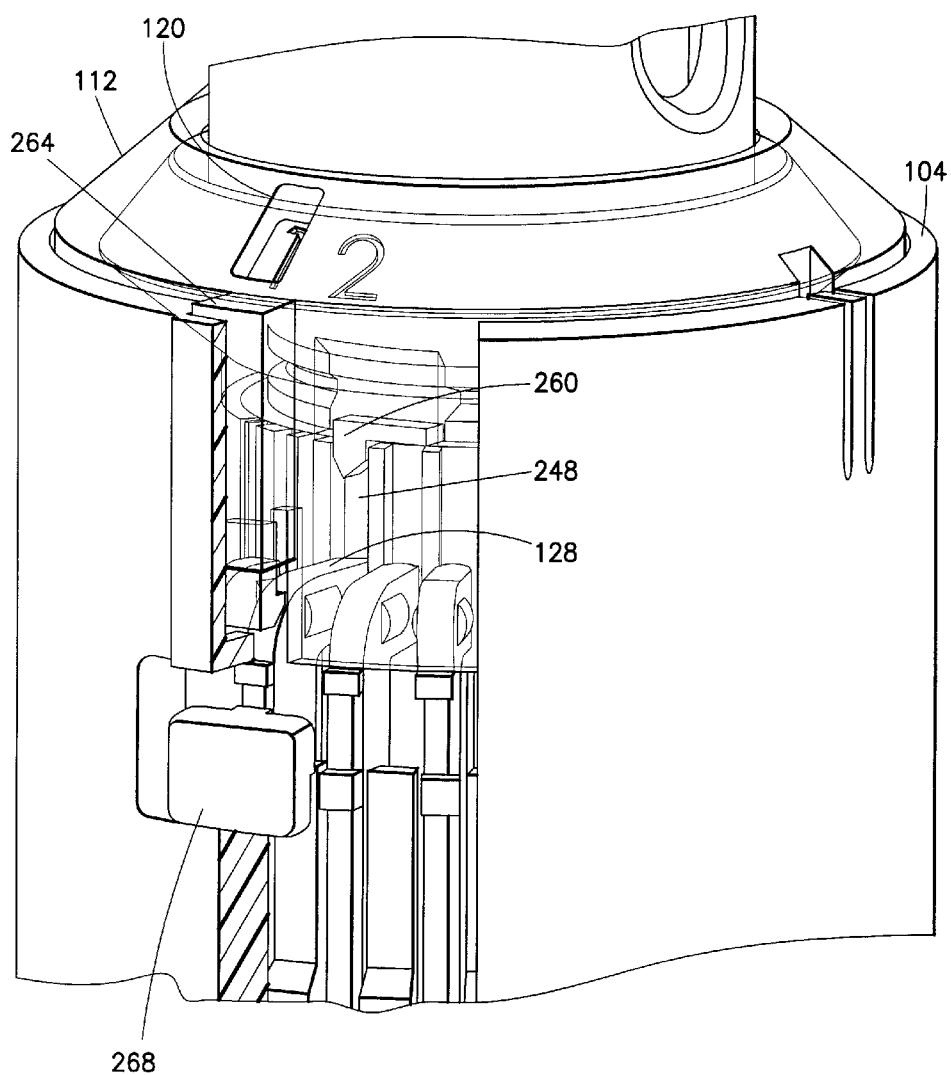

Operation of the changing device 100 will now be discussed in more detail with respect to FIGS. 17-29. As shown in FIG. 17, the needle holder 124 includes a plurality of axial slots 248 arrayed radially around the needle holder 124. The counter ring retainer 112 includes an anti-rotation member 252. According to one embodiment, the anti-rotation member 252 comprises a cantilevered arm 256 having a locking head 260 disposed at a free end thereof. The outer housing 104 is coupled with a protrusion 264 (see, for example, FIG. 4) of the counter ring retainer 112 so that the counter ring retainer 112 rotates along with the outer housing 104. As the user rotates the outer housing 104 to select the next unused needle 128, the anti-rotation member 252 slides into the axial slot 248 corresponding to the next unused needle 128. More specifically, under the bias of the cantilevered arm 256, the locking head 260 slides into and engages the axial slot 248, as shown in FIG. 18. The engagement of the locking head 260 with the axial slot 248 prevents circumferential rotation of the outer housing 104 and the counter ring retainer 112.

Figure 19:
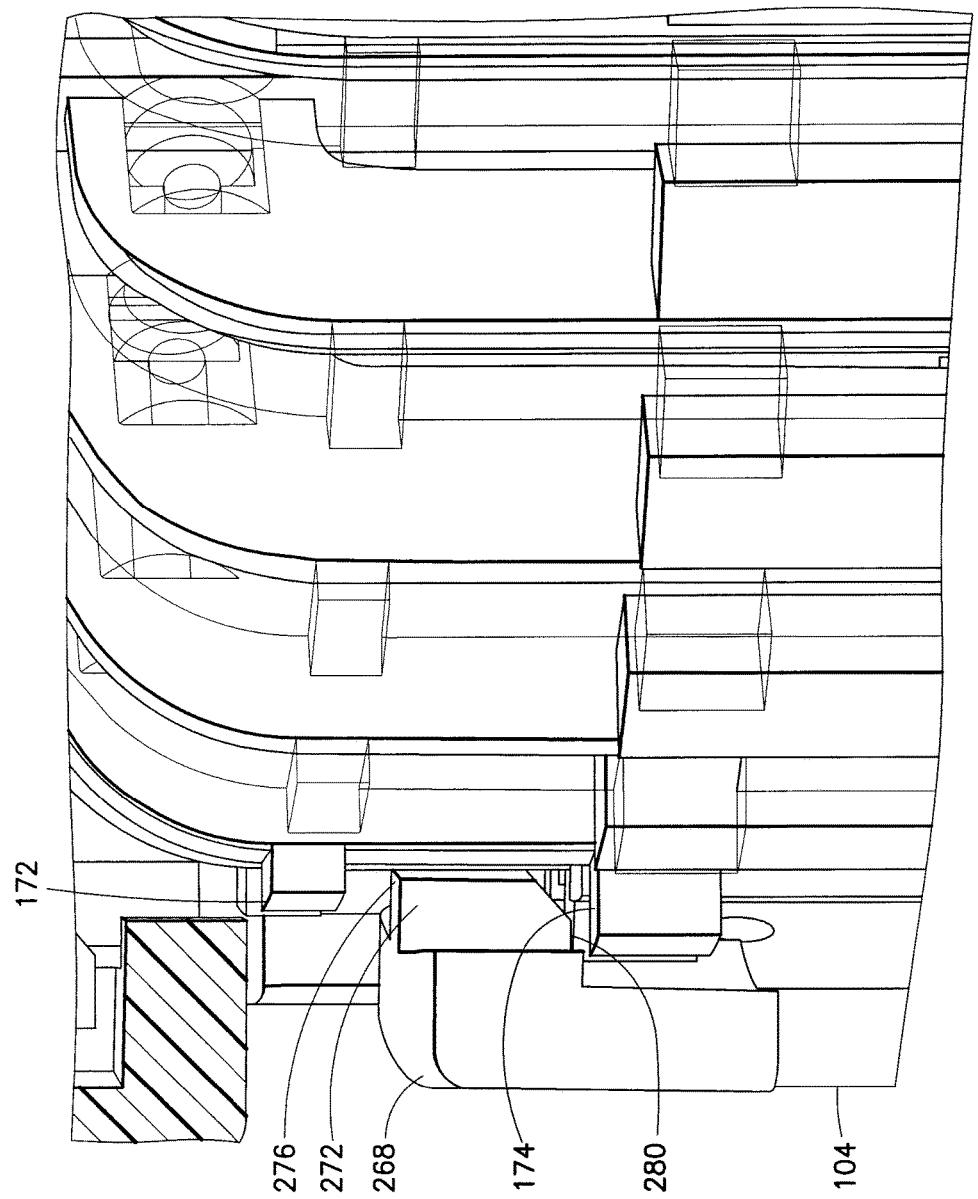
Figure 20:
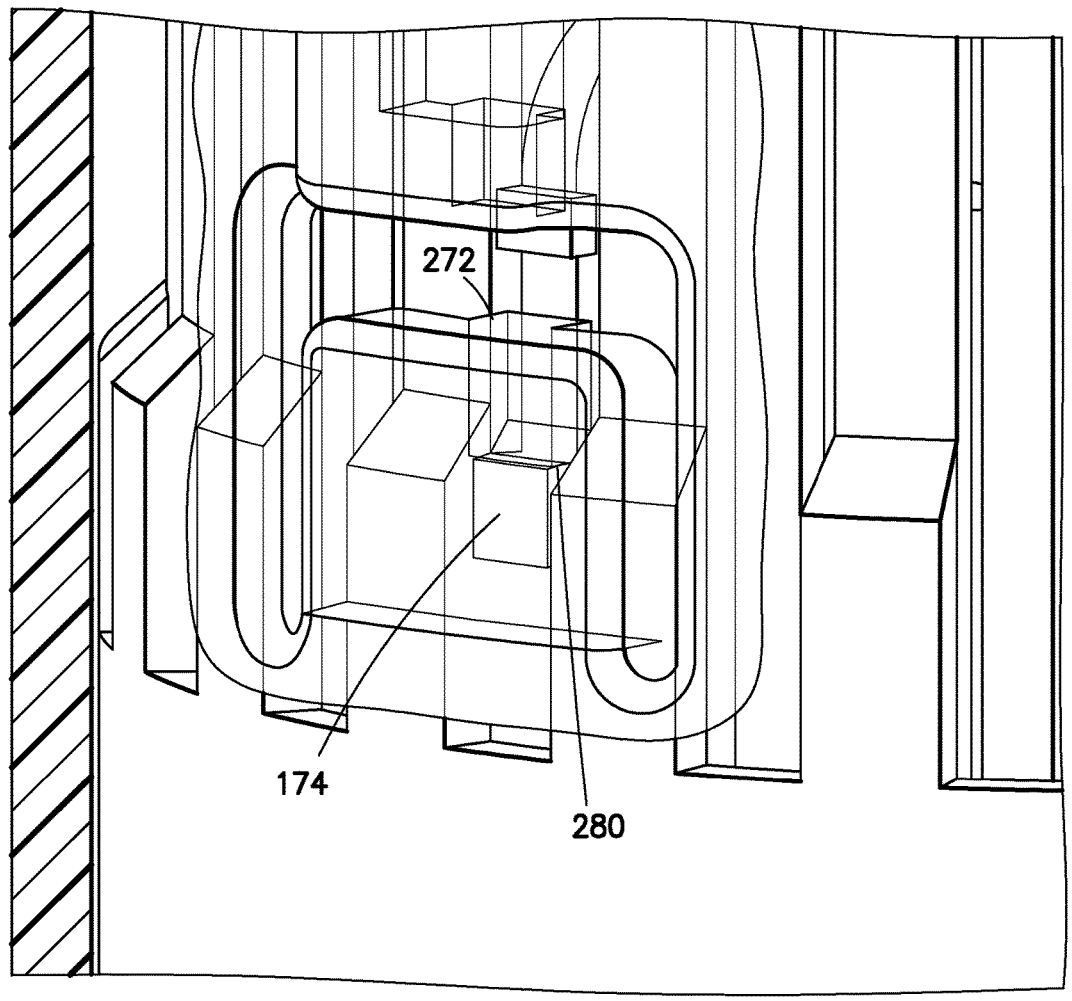

Also shown in FIG. 18 (as well as FIG. 3), the outer housing 104 includes an engagement arm 268 for selectively engaging portions of the needle 128. As shown in FIG. 19, the engagement arm 268 has a tooth 272. The tooth 272 has a top 276 and a bottom 280. The top 276 is substantially flat and the bottom 280 has a flat portion and a beveled portion. As the user moves the outer housing axially away from the pen injector 50, as shown in FIG. 20, the flat portion of the bottom 280 of the tooth 272 engages the top of lower needle protrusion 174 (also shown in FIG. 6) and thereby drives the needle 128 axially away from the pen injector 50. This axial motion of the needle 128 causes the septum penetrating portion 164 of the needle 128 to penetrate all the way through the reservoir septum 132 into the reservoir 148.

Figure 21:
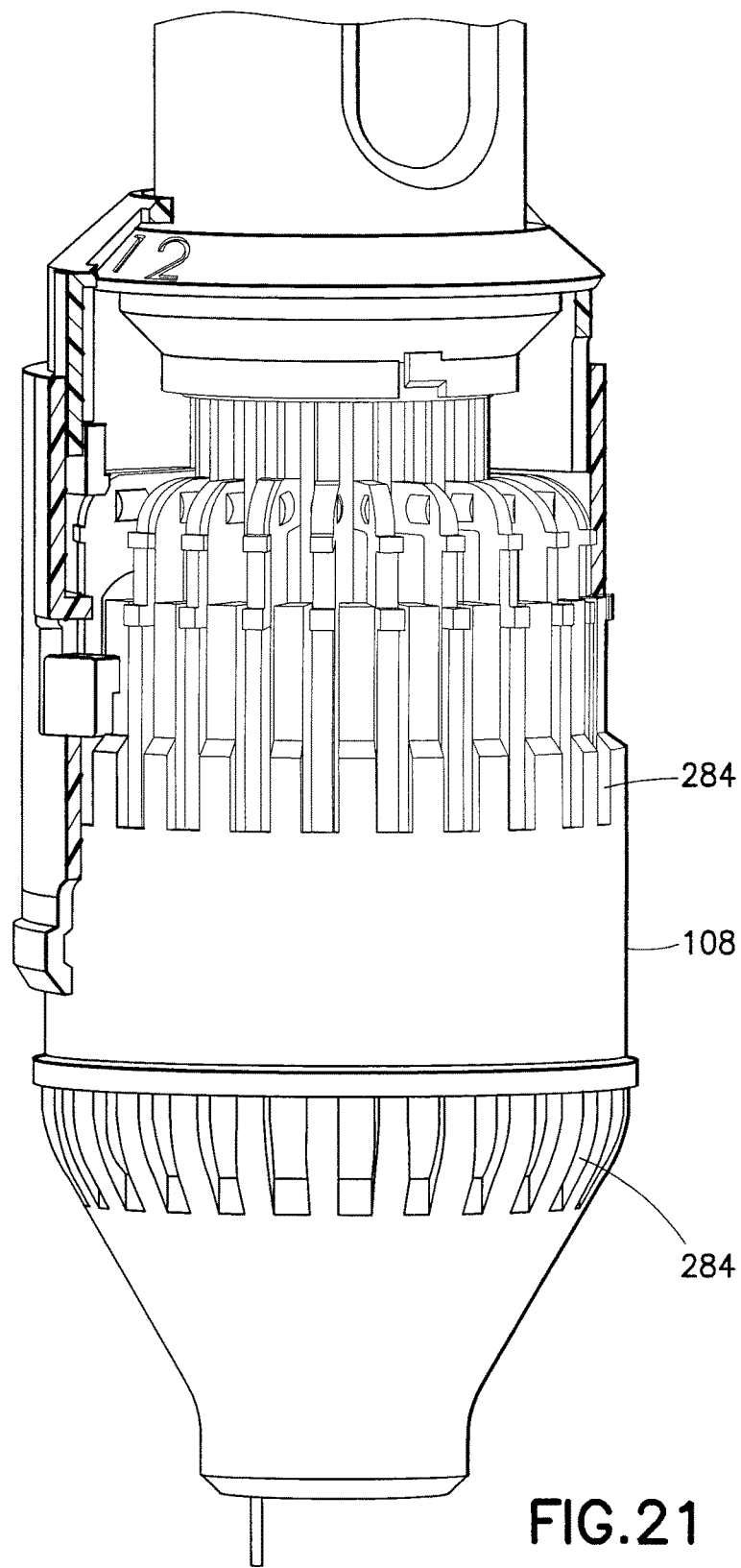

Additionally, this axial motion of the needle 128 causes the patient portion 160 of the needle 128 to penetrate all the way through the patient end septum 140 and extend outside of the changing device 100, as shown in FIG. 21. Thus, the axial stroke of the outer housing 104 established fluid connection between the patient portion 160 and the reservoir 148. According to one embodiment, the patient portion 160 of the needle 128 has a lubricant disposed thereon for easing injection into a patient. Also illustrated in FIG. 21, the inner housing 108 includes a plurality of slots 284 to guide axial movement of the needle 128. Additionally, the exposed patient portion 160 of the needle 128 is radially displaced with respect to a center of the changing device 100. In other words, the exposed patent portion of the needle 128 is offset from the center.

Figure 22:
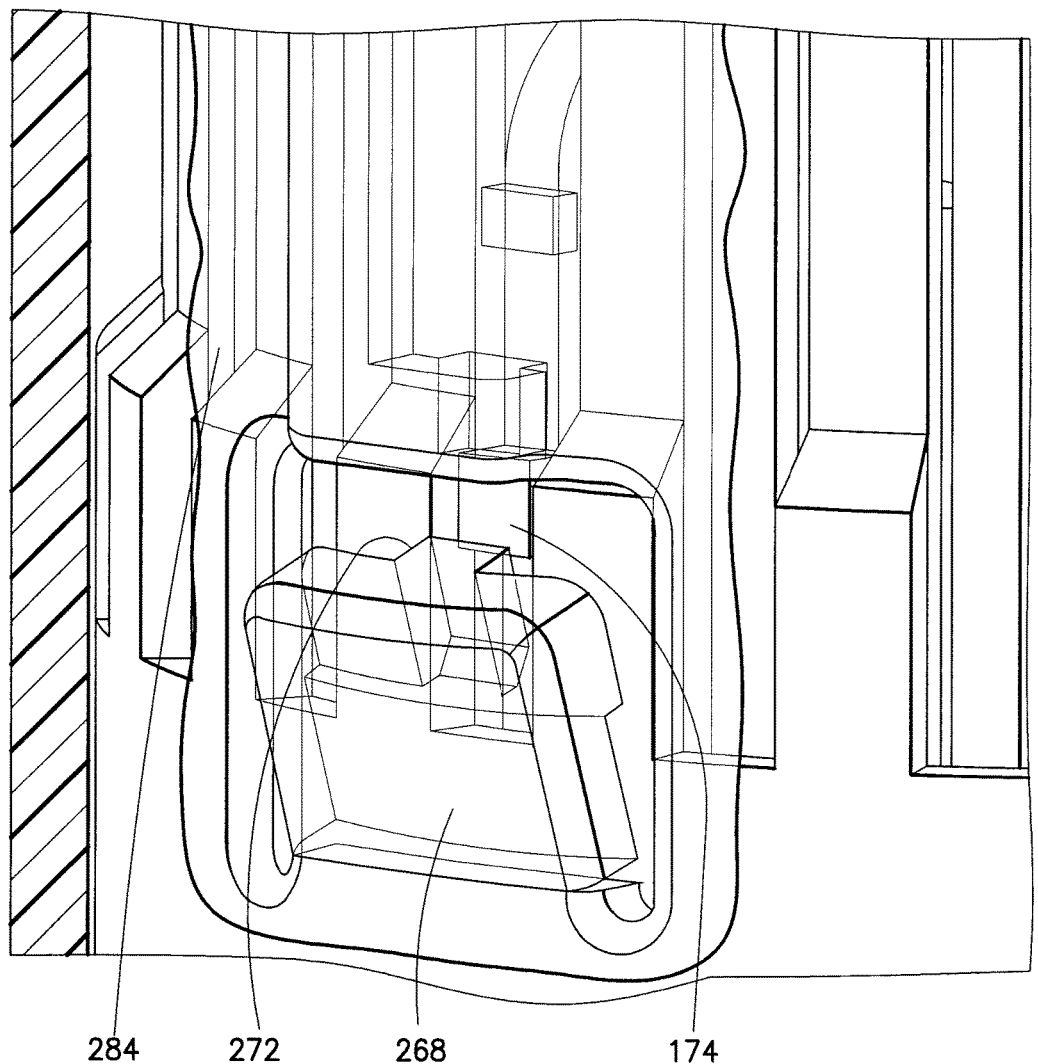
Figure 23:
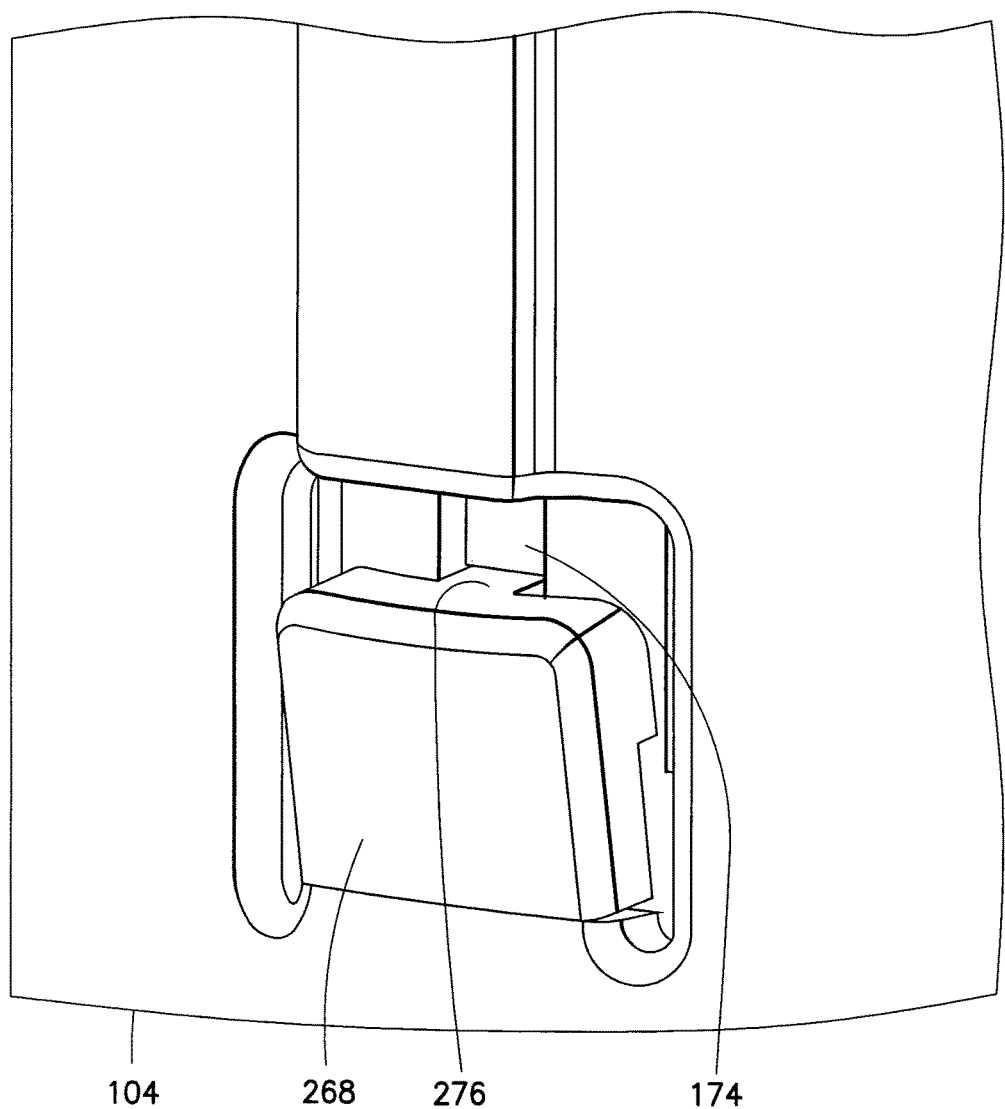

Once the patient portion 160 of the needle 128 is completely extended, as the user continues to move the outer housing 104 axially away from the pen injector 50, as shown in FIG. 22, the beveled portion of the bottom 280 of the tooth 272 causes the tooth 272 of the engagement arm 268 to slide over the lower needle protrusion 174. Once the tooth 272 clears the bottom of the lower needle protrusion 174, the cantilevered engagement arm 268 snaps back radially inwardly so that the top 276 of the tooth 272 engages the bottom of the lower needle protrusion 174, as shown in FIG. 23.

On the first use of the changing device 100, the user primes the device 100 to express one, or a few drops of the medicament from the patient portion 160 of the needle 128, to test the fluid path and to ensure that there are no air bubbles in the fluid path. This priming charges the chamber 148, and thus further priming during the use of the device 100 is substantially unnecessary. To minimize wasting medicament during priming, the volume of the reservoir 148 is minimized. Once the outer housing 104 reaches the bottom of its stroke, the user injects the desired volume of medicament.

Figure 24:
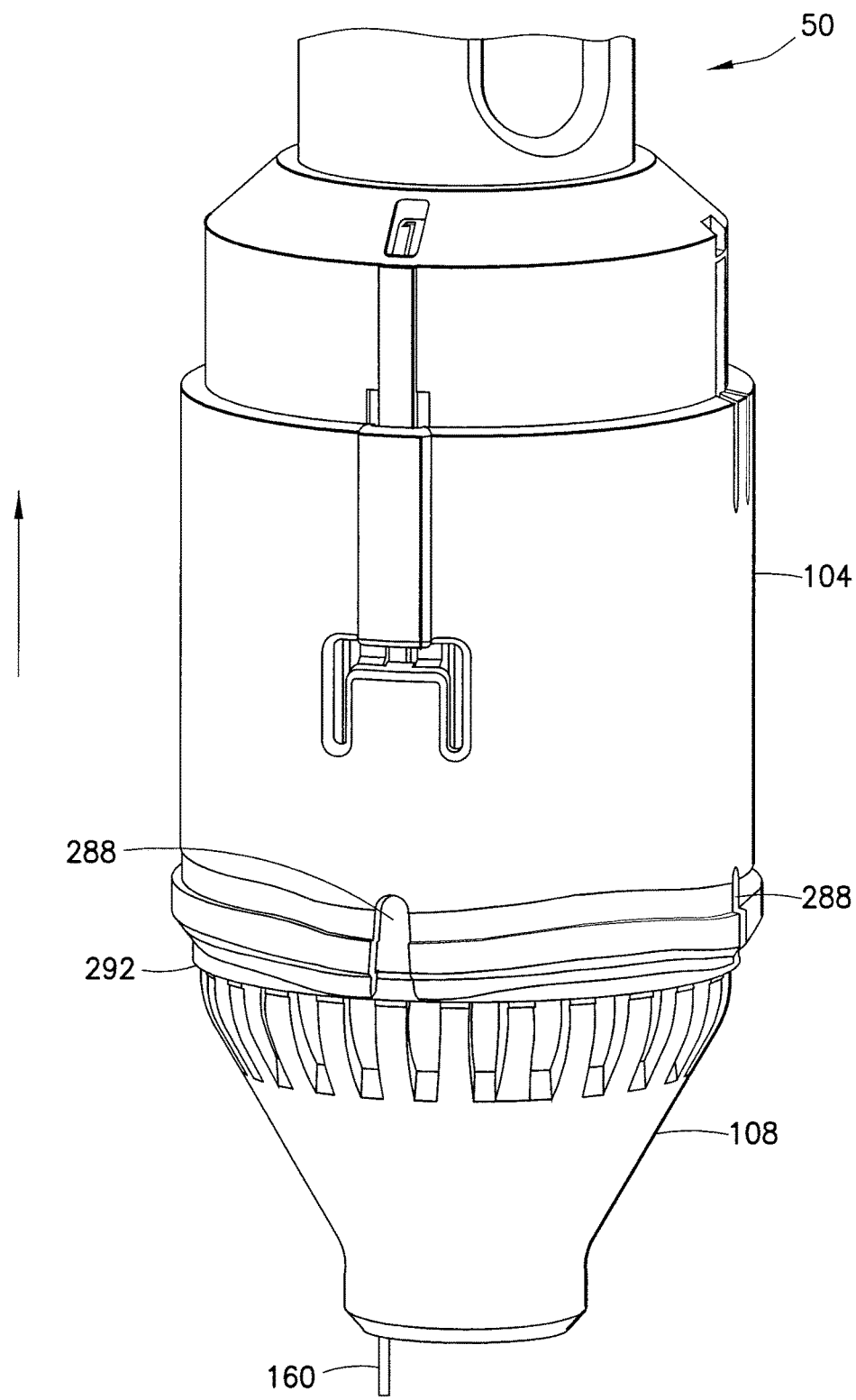

As shown in FIG. 24, a lower portion of the outer housing 104 has a plurality of relief slots 288 so that as the outer housing 104 reaches the bottom of its stroke, the lower portion of the outer housing 104 passes over a circumferential hub 292 of the inner housing 108 and elastically deforms radially outwardly. This elastic deformation biases the outer housing 104 to ease the subsequent upward motion (axially toward the pen injector 50) of the outer housing 104.

Subsequent to administering the medicament, the user moves the outer housing 104 axially toward the pen injector 50 to re-sheath the patient portion 160 of the needle 128 within the patient end septum 140 and displace the septum penetrating portion 164 relative to the reservoir septum 132, so that the septum penetrating portion 164 of the needle 128 no longer extends into the reservoir 148.

Figure 25:
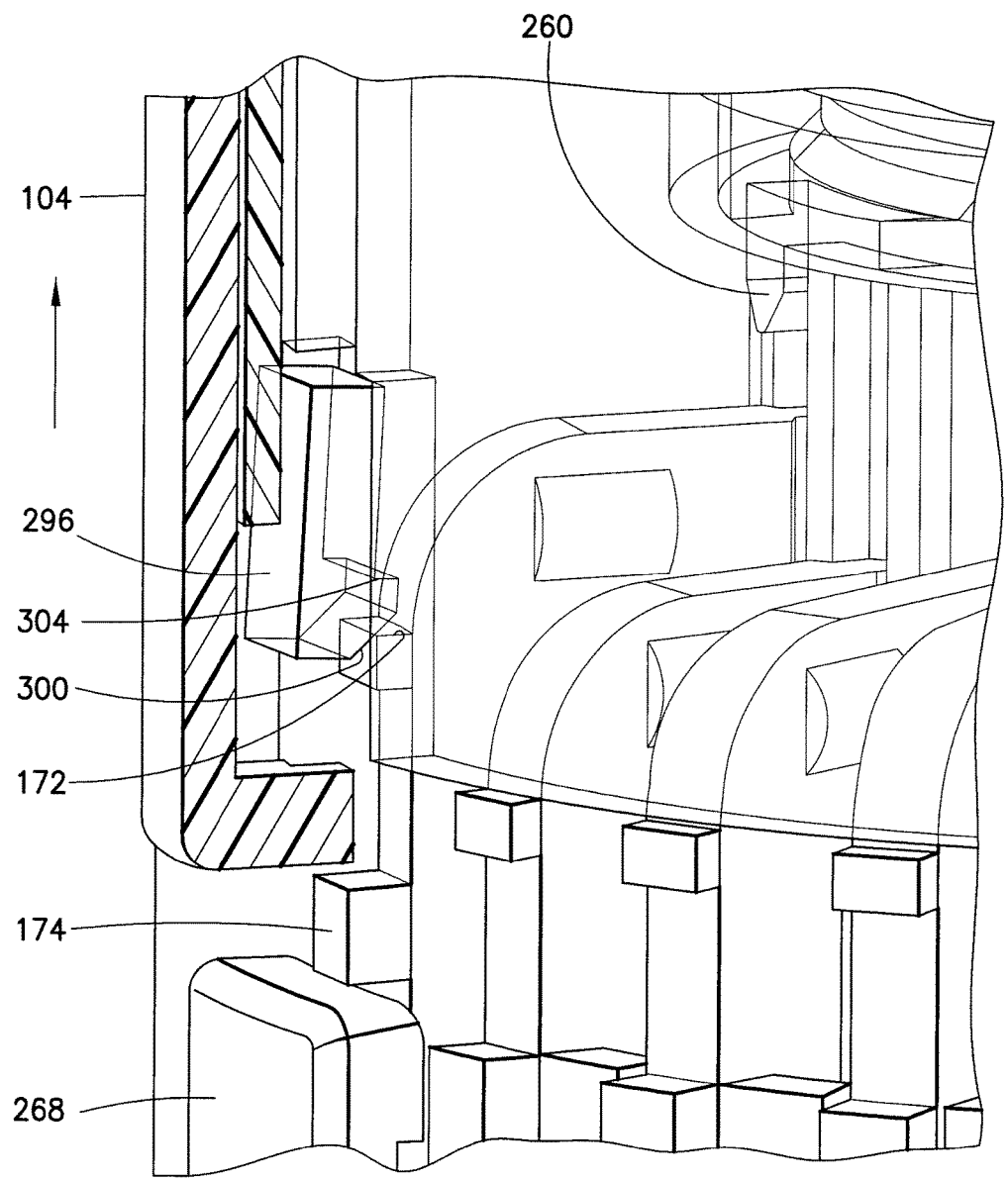

Turning to FIG. 25, as the user moves the outer housing 104 axially toward the pen injector 50, due to engagement between the engagement arm 268 and the bottom of the lower needle protrusion 174, the top of upper needle protrusion 172 engages a lower portion 296 of the protrusion 264 of the counter ring retainer 112. According to one embodiment, the lower portion 296 of the protrusion 264 is cantilevered. As shown in FIG. 25, the lower portion 296 has a beveled portion 300 and a retaining portion 304. As the outer housing 104 moves the needle 128 axially toward the pen injector 50, the top of the upper needle protrusion 172 engages the beveled portion 300, deflecting (i.e., elastically deforming) the protrusion 264 to displace the lower portion 296 radially outwardly.

Figure 26:
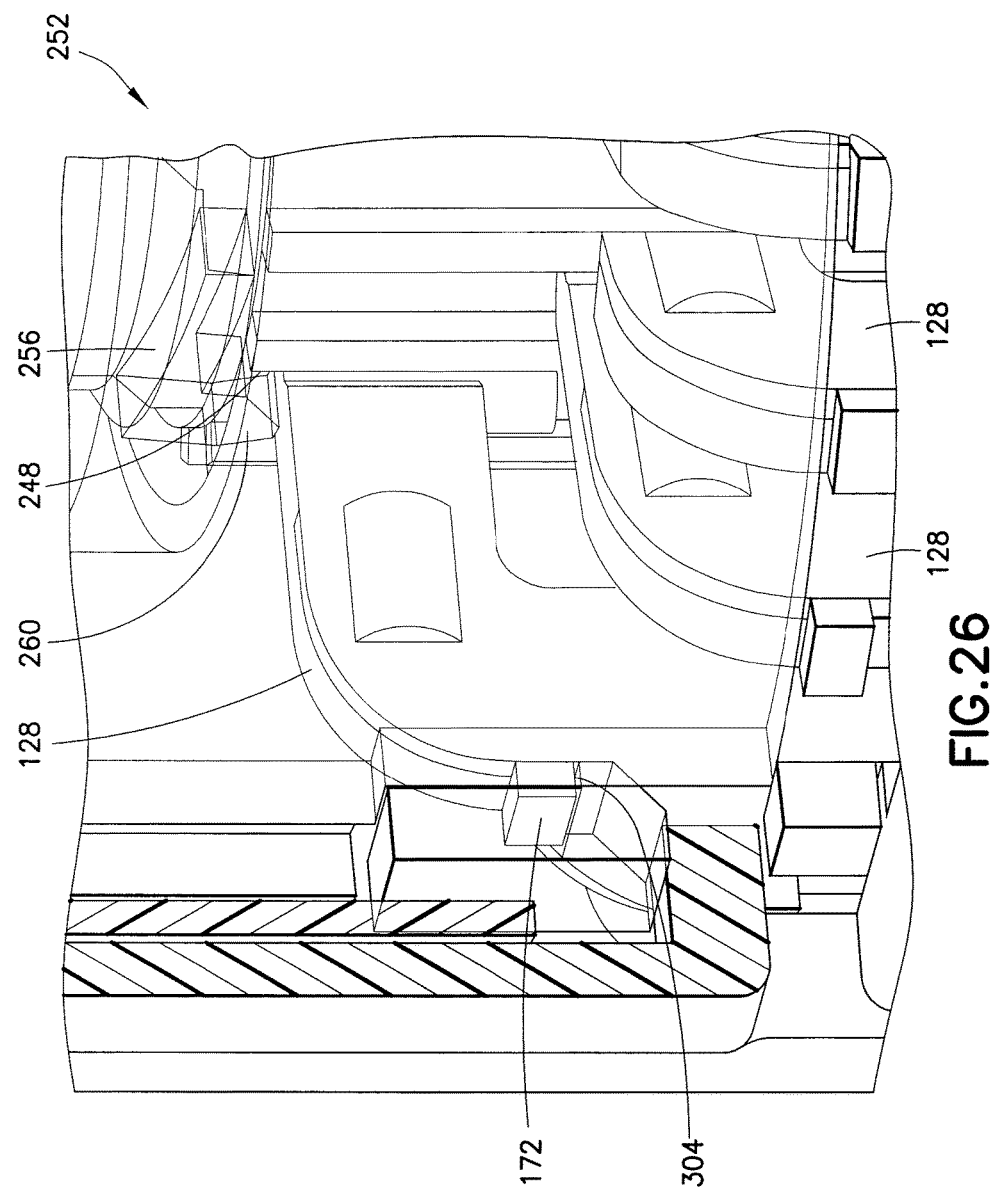

With further axial upward motion of the needle 128, as the outer housing 104 reaches the top of its stroke, the upper needle protrusion 172 passes the lower portion 296 of the protrusion 264, which snaps back radially inwardly to so that the retaining portion 304 engages the bottom of the upper needle protrusion 172, as shown in FIG. 26. Additionally, this further axial upward motion of the needle 128 causes the top of the needle 128 to engage and displace the locking head 260 of the anti-rotation member 252 of the counter ring retainer 112, thereby disengaging the locking head 260 from its locked position with respect to the axial slot 248.

Figure 27:
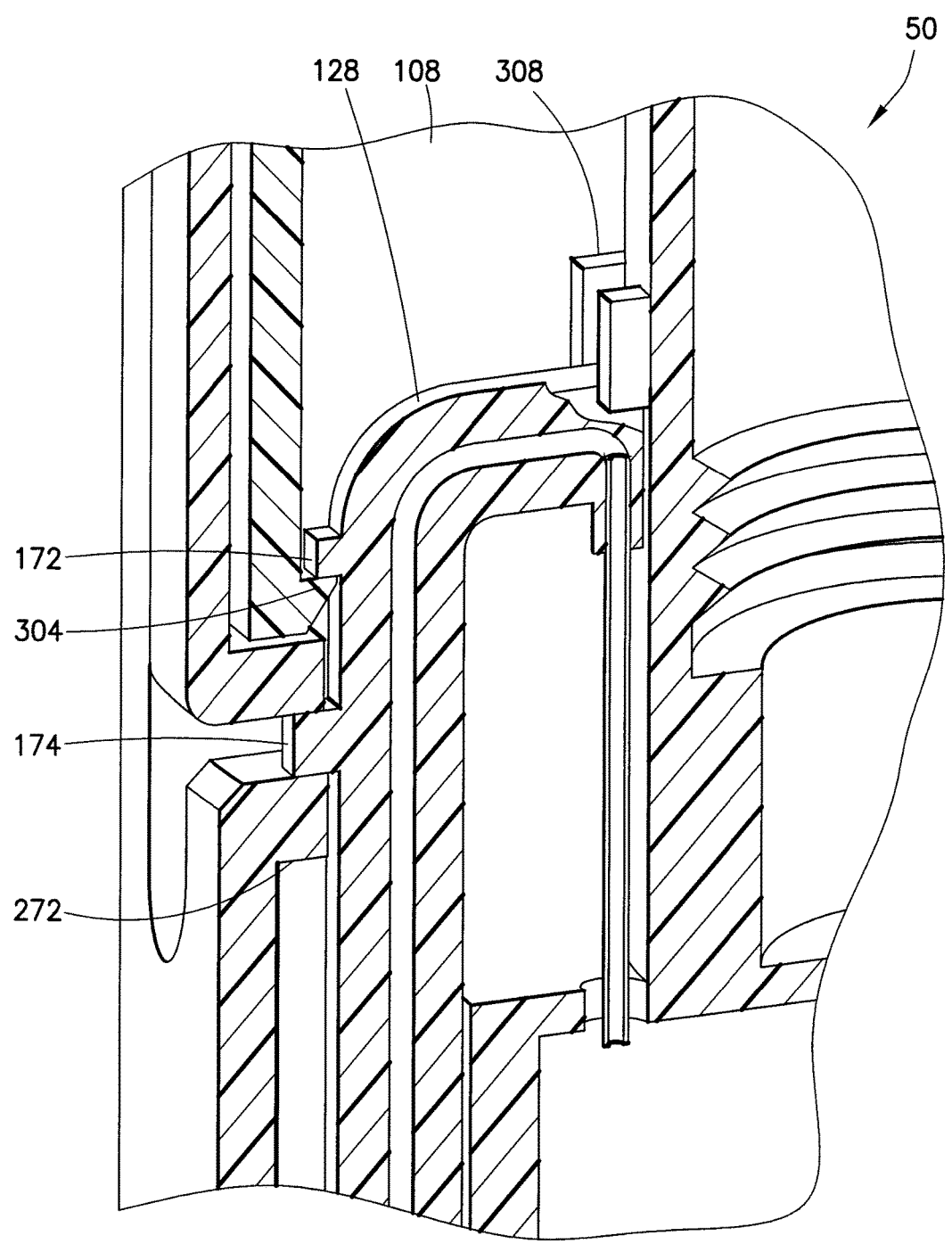

Further, though omitted from FIG. 26 for clarity, as shown in FIG. 27, as the outer housing 104 reaches the top of its stroke, the top of the needle 128 is retained by a retaining clip 308 of the inner housing 108 to retain the used needle 128 in an axially raised position with respect to the remaining unused needles 128 (see FIG. 26 for relative positioning of used needle 128 and unused needles 128). Retention of the needle 128 by the retaining clip 308 prevents the needle 128 from being selected as the next unused needle, and thereby prevents reuse of the needle 128.

Figure 28:
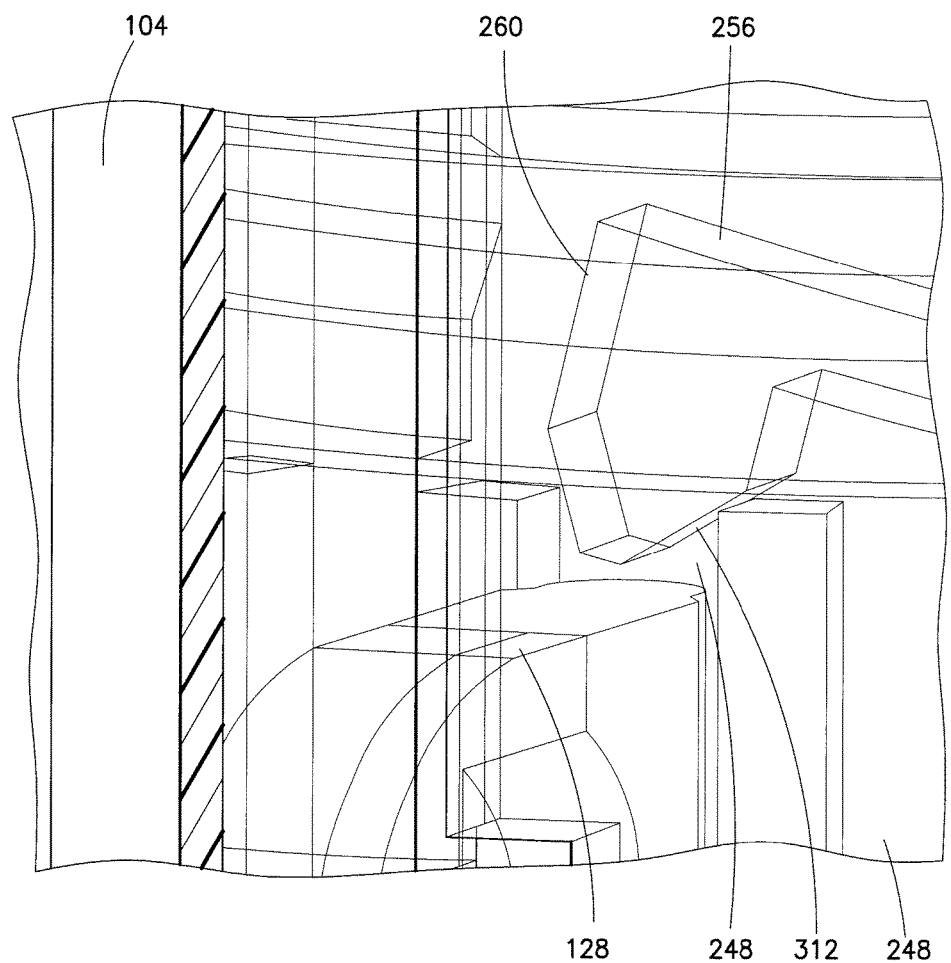
Figure 29:
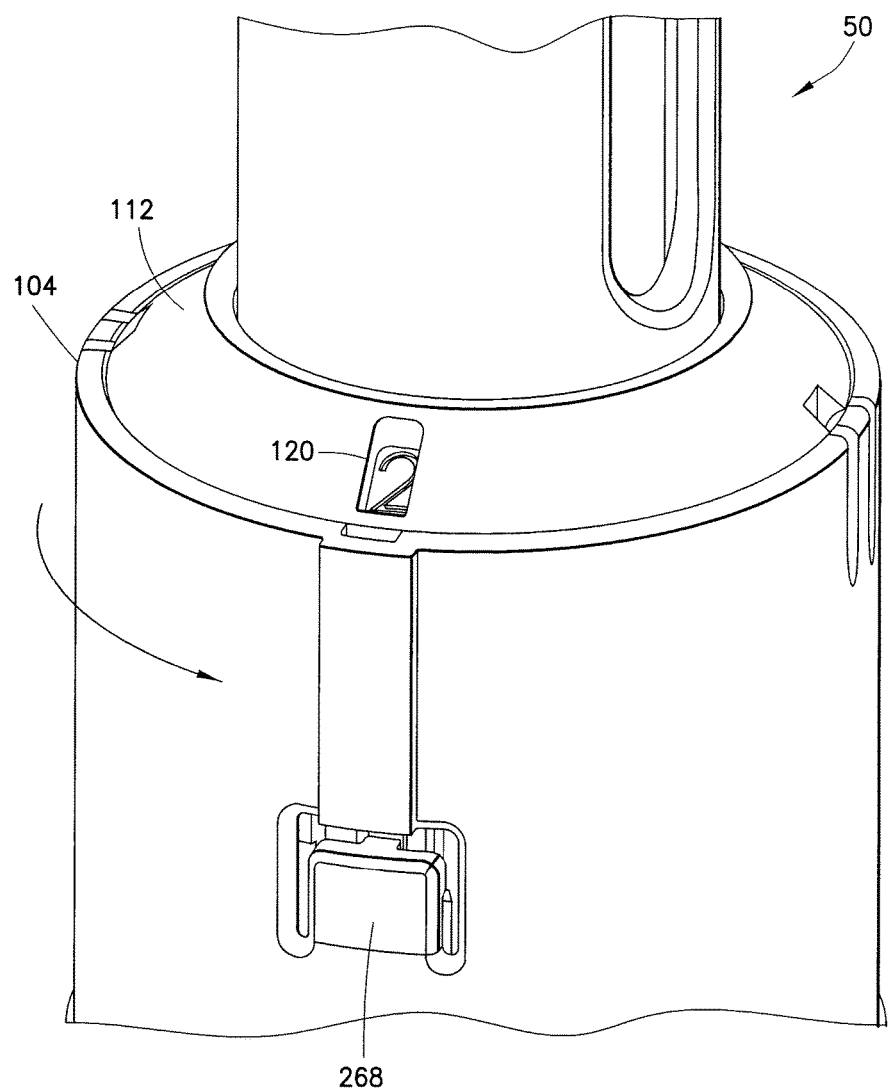

Referring to FIG. 28, because the locking head 260 has been freed from the locking position with respect to the axial slot 248 by the upward axial movement of the needle 128, the user is once again permitted to circumferentially rotate the outer housing 104 and the counter ring retainer 112. When the user rotates the outer housing 104 and the counter ring retainer 112, a beveled face 312 of the locking head 260 contacts the side of the axial slot 248, moving the locking head upward and energizing the cantilevered arm 256. Once the locking head 260 clears the edge of the axial slot 248, continued rotation of the outer housing by the user moves the anti-rotation member 252 to the next axial slot, to select the next unused needle 128, as shown in FIG. 29.

According to one embodiment, the user rotates the outer housing 104 approximately 15° to select the next unused needle 128. One skilled in the art will understand, however, that other increments of rotation may be employed without departing from the scope of the invention. Additionally, although in the above-described embodiment adjacent needles 128 are sequentially selected, one skilled in the art will understand that sequentially selected needles need not be adjacent. For example, every other, or every third needle 128 may be selected as the next unused needle to permit a greater range of rotation of the outer housing to accommodate a desired patient feel to the patient interface. In such an embodiment, two or three full rotations of the outer housing may be used to exhaust all the unused needles. Numbering of the needles on the needle counter would, of course, need to be altered appropriately.

Further, although, the numbering system in the above-described embodiment counts upward with respect to the number of needles, it will be understood that the changing device 100 may, without departing from the scope of the present invention, count downward, reflecting the number of unused needles remaining.

FIGS. 30 and 31 are perspective views in cross-section of a first alternative sterility barrier for the changing device 100. As shown in FIG. 30, a respective plurality of tubes 316 is disposed around bottom portions of the plurality of needles 128. An inner septum 320 is disposed at a bottom of the inner housing 108, and a non-resealing membrane 324 covers the bottom of the inner septum 320. The inner septum 320 has an annular snap 328 that secures the inner septum 320 within a guide 332. The guide 332 has holes therethrough to guide the tubes 316 when they pass through the guide 332.

In operation, prior to deployment, each tube 316 covers a part of the needle 128 that does not penetrate skin so that the sterile patient portion 160 is only exposed to air. Upon deployment, the tube 316 moves down along with the needle 128 as the needle 128 is exposed outside of the changing device 100. The bottom of the tube 316 remains embedded in the inner septum 320 as the patient portion 160 continues its downward movement to pierce the membrane 324 and be exposed outside the changing device 100. Subsequently, as the needle 128 is moved axially toward the pen injector 50, as shown in FIG. 31, the tube 316 remains embedded in the inner septum 320, shielding the unused needles from being contaminated.

Figure 32:
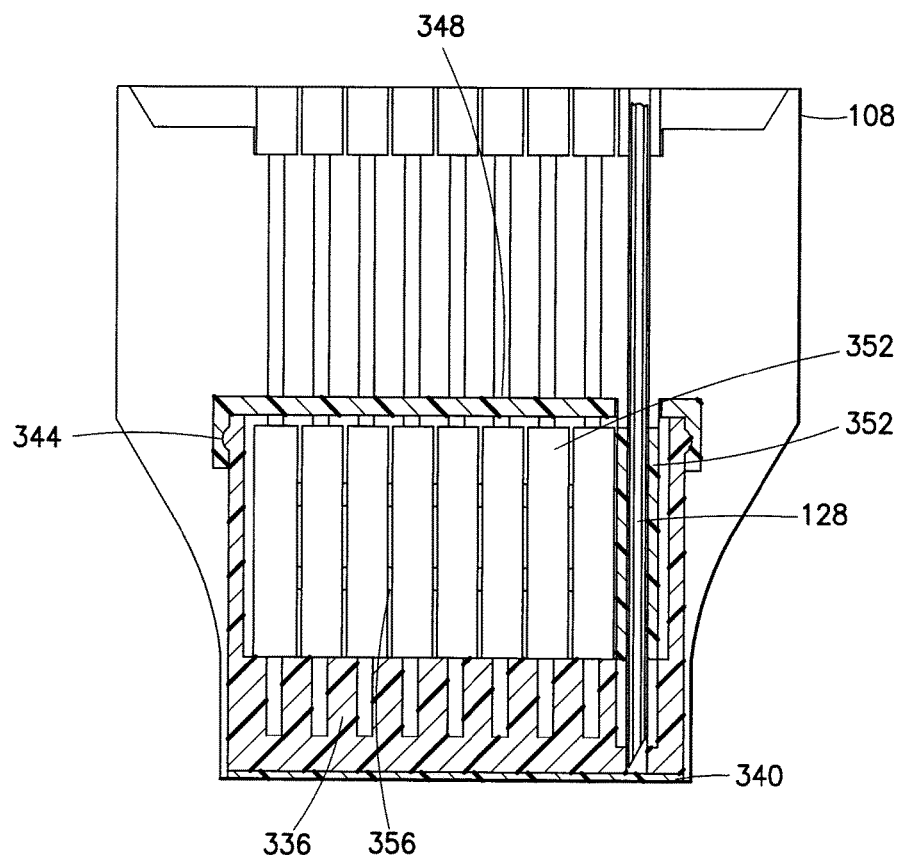
FIG. 32 is a perspective view in cross-section of a second alternative sterility barrier for the needle changing device of FIG. 3.

FIG. 32 is a perspective view in cross-section of a second alternative sterility barrier for the changing device 100. Similar to the embodiment of FIGS. 30 and 31, an inner septum 336 is disposed at a bottom of the inner housing 108, and a non-resealing membrane 340 covers the bottom of the inner septum 336. Additionally, the inner septum 336 has an annular snap 344 that secures the inner septum 336 within a guide 348. The guide 348 has holes therethrough to guide the needles 128. Further, a plurality of tubes 352 corresponds to the plurality of needles 128. The tubes 352, however, are connected by at least one band 356, and are fixedly disposed in the inner septum 336. Because the tubes 352 are fixedly disposed in the inner septum 336, the tubes 352 shield the unused needles 128 from being contaminated. In operation, the needles 128 move relative to the fixed tubes 352.

FIG. 33 is a perspective view in cross-section and FIG. 34 is a perspective view, together illustrating a third alternative sterility barrier for the changing device 100. As shown in FIG. 33, the patient portion 160 of the needle 128 is housed within a hollow cylinder 360 that contacts a soft septum 364 on the bottom of the inner housing 108. Upon activation, as shown in FIGS. 33 and 34, the cylinder 360 pierces through the membrane or septum 364, opening a path for the patient portion 160 to be exposed. The patient portion 160 does not contact the cylinder 360. According to one embodiment shown in FIG. 34, the septum 364 has a + or x-shaped (cruciform) perforation to ease the piercing.

FIGS. 35 and 36 are perspective views in cross-section of a fourth alternative sterility barrier for the changing device 100. As shown in FIG. 35, a plurality of sharp features 368 is disposed on a floor of the inner housing 108. The floor of the inner housing 108 has a hole 370 therethrough corresponding to the interior of each sharp feature 368. The sterility barrier around the patient portion 160 is a rigid plastic shell 372 that does not contact the patient portion 160. The rigid plastic shell 372 may be made of, for example, PE or PP. In operation, as shown in FIG. 36, as the user moves the needle 128 axially away from the pen injector 50 via the outer housing 104, the sharp feature 368 pierces the shell 372 and the patient portion 160 extends through the hole 370.

Figure 37:
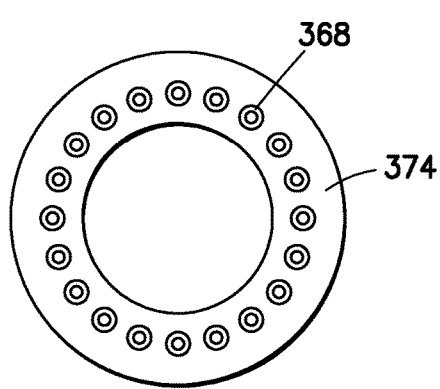
FIG. 37 is a perspective view of a septum plate.
Figure 38:
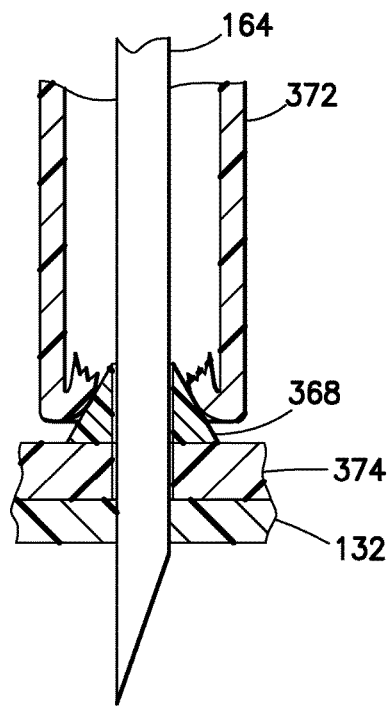
FIG. 38 is a perspective view in cross-section of the fourth alternative sterility barrier for the needle changing device of FIG. 3 employing the septum plate of FIG. 37.
Figure 39:
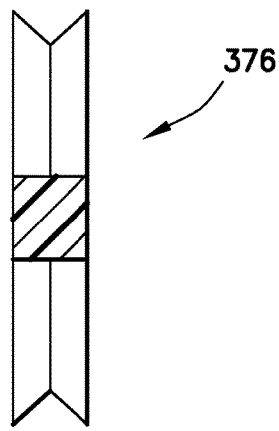
Figure 40:
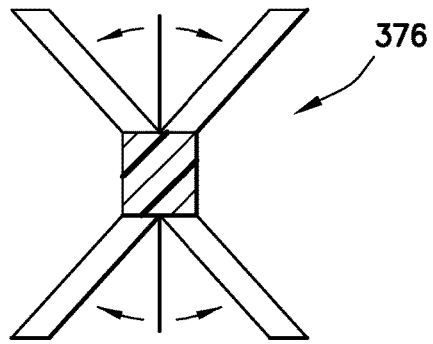

According to one embodiment, the sharp features 368 and shell 372 are similarly applied to the septum penetrating portion 164. For example, as shown in FIG. 37, an annular septum plate 374 disposed on top of reservoir septum 132 has a plurality of sharp features 368 disposed thereon. In this embodiment, the sharp features are frusta, or truncated cones. One skilled in the art will understand that other shapes are possible for the sharp features without departing from the scope of the invention. In operation, as shown in FIG. 38, as the user moves the needle 128 axially away from the pen injector 50 via the outer housing 104, the sharp feature 368 pierces the shell 372 and the septum penetrating portion 164 extends into and through the self-sealing reservoir septum 132.

FIGS. 39-42 are perspective views in cross-section of a fifth alternative sterility barrier for the changing device 100. FIGS. 39-42 illustrate a rigid plastic sterility barrier 376 that breaks part during needle engagement with the floor of the inner housing 108. The rigid plastic barrier 376 may be made of, for example, PE or PP. According to one embodiment, the barrier 376 is integral to a hub of the patient portion 160 via living hinges. According to one embodiment, the sterility barrier 376 is similarly applied to the septum penetrating portion 164, with the reservoir septum 132 functioning in a similar manner to the floor of the inner housing 108, except that there is no pre-existing hole in the reservoir septum 132.

FIGS. 43 and 44 are perspective views in cross-section of a sixth alternative sterility barrier for the changing device 100. As shown in FIG. 43, the patient portion 160 has a hub 380 disposed thereon, and the hub 380 has a sterility barrier 384 slidably disposed thereon. In operation, as shown in FIG. 44, as the barrier 384 contacts the floor of the inner housing 108 when the user moves the needle 128 axially away from the pen injector 50 via the outer housing 104, the barrier 384 collapses by sliding up the hub 380. As the barrier 384 collapses, the patient portion 160 pierces through the barrier 384 and extends through a hole 388 in the floor of the inner housing 108. According to one embodiment, the hub 380 and barrier 384 are similarly applied to the septum penetrating portion 164, with the reservoir septum 132 functioning in a similar manner to the floor of the inner housing 108, except that there is no pre-existing hole in the reservoir septum 132.

Figure 45:
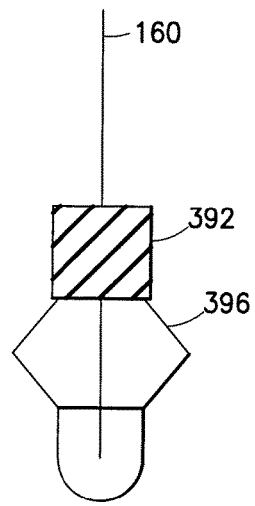
FIGS. 45 and 46 are perspective views in cross-section of a seventh alternative sterility barrier for the needle changing device of FIG. 3.
Figure 46:
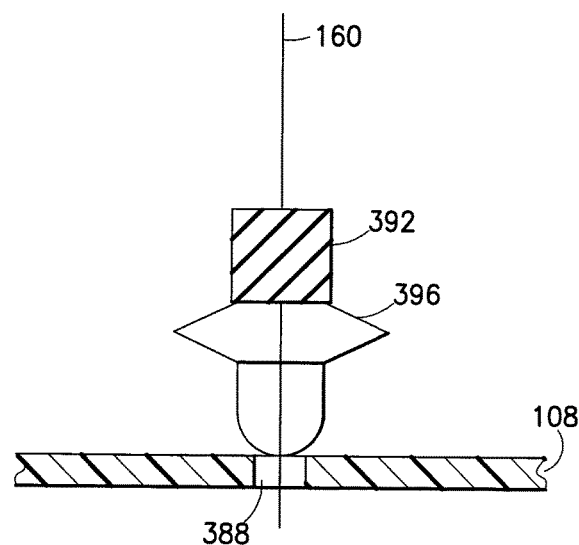

FIGS. 45 and 46 are perspective views in cross-section of a seventh alternative sterility barrier for the changing device 100. As shown in FIG. 45, the patient portion 160 has a hub 392 disposed thereon, and the hub 392 has a sterility barrier 396 disposed thereon. In operation, as shown in FIG. 46, as the barrier 396 contacts the floor of the inner housing 108 when the user moves the needle 128 axially away from the pen injector 50 via the outer housing 104, the barrier 396 collapses and the patient portion 160 pierces through the barrier 396, extending through the hole 388 in the floor of the inner housing 108. According to one embodiment, the hub 392 and barrier 396 are similarly applied to the septum penetrating portion 164, with the reservoir septum 132 functioning in a similar manner to the floor of the inner housing 108, except that there is no pre-existing hole in the reservoir septum 132.

Figure 47:
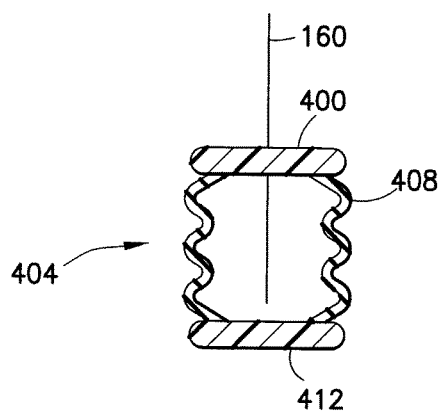
FIGS. 47 and 48 are perspective views in cross-section of an eighth alternative sterility barrier for the needle changing device of FIG. 3.
Figure 48:
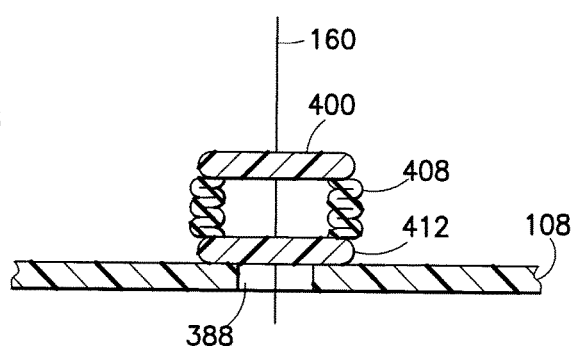

FIGS. 47 and 48 are perspective views in cross-section of an eighth alternative sterility barrier for the changing device 100. As shown in FIG. 47, the patient portion 160 has a hub 400 disposed thereon, and the hub 400 has a sterility barrier 404 disposed thereon. The barrier 404 includes a bellows 408 and an end piece 412. According to one embodiment, the end piece 412 is made of paper. In operation, as shown in FIG. 48, as the barrier 404 contacts the floor of the inner housing 108 when the user moves the needle 128 axially away from the pen injector 50 via the outer housing 104, the bellows 408 collapses and the patient portion 160 pierces through the end piece 412, extending through the hole 388 in the floor of the inner housing 108. According to one embodiment, the sterility barrier 404 is similarly applied to the septum penetrating portion 164, with the reservoir septum 132 functioning in a similar manner to the floor of the inner housing 108, except that there is no pre-existing hole in the reservoir septum 132.

Figure 49:
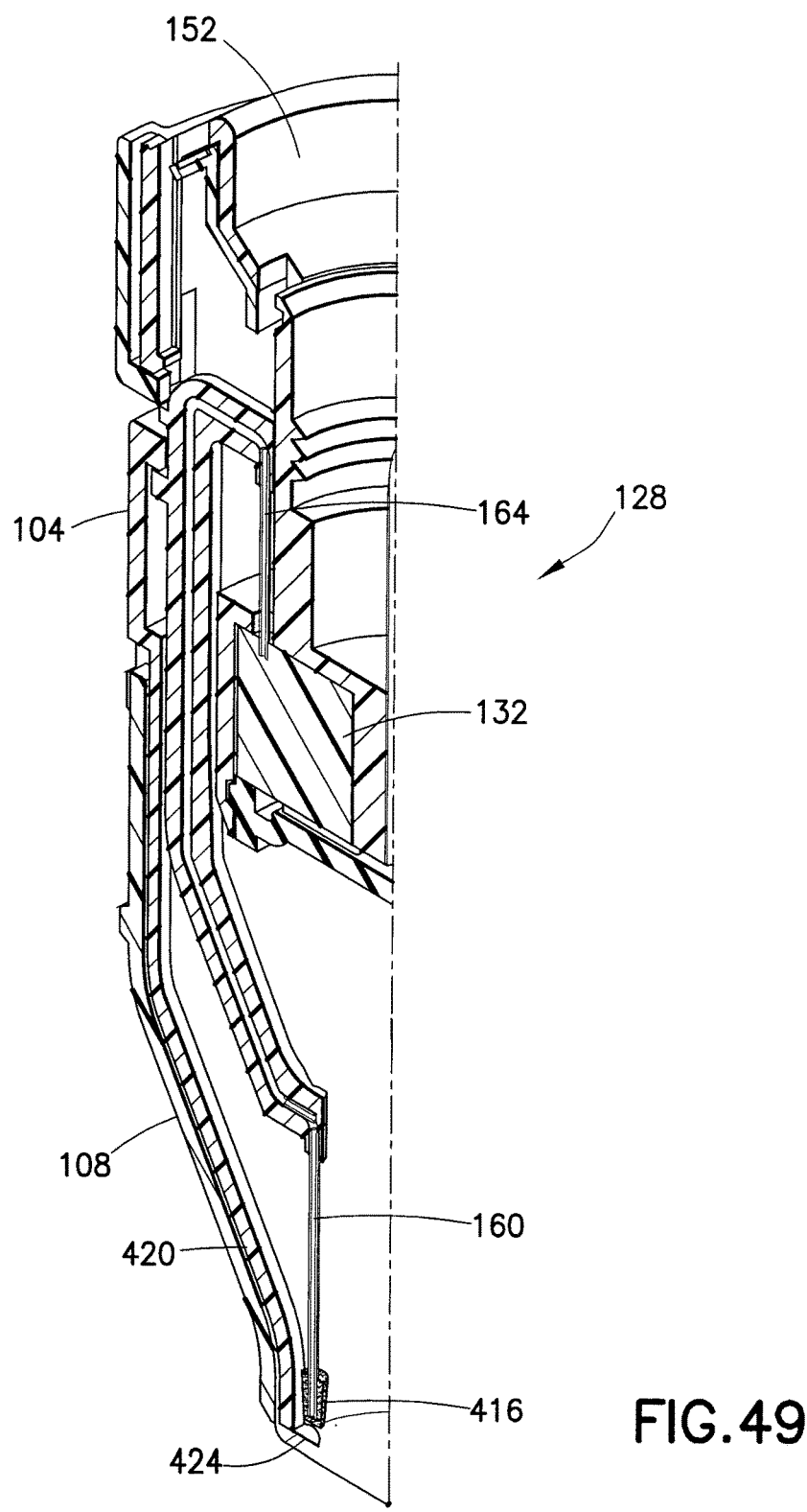
FIG. 49 is a partial perspective view in cross-section of a ninth alternative sterility barrier for the needle changing device of FIG. 3.

FIG. 49 is a partial perspective view in cross-section of a ninth alternative sterility barrier 416 for the changing device 100, in which the sterility barrier 416 is cut away during rotation of the outer housing 104. According to one embodiment, the barrier 416 is a paper barrier 416. As shown in FIG. 49, the outer housing 104 has a cutting arm 420 extending down into the inner housing 108. For clarity, only a single needle 128 is shown. The cutting arm 420 has a blade 424 disposed at a distal end thereof. During rotation of the outer housing 104, the blade slices open, or peels off the sterility barrier 416 of the next unused needle 128.

Figure 50:
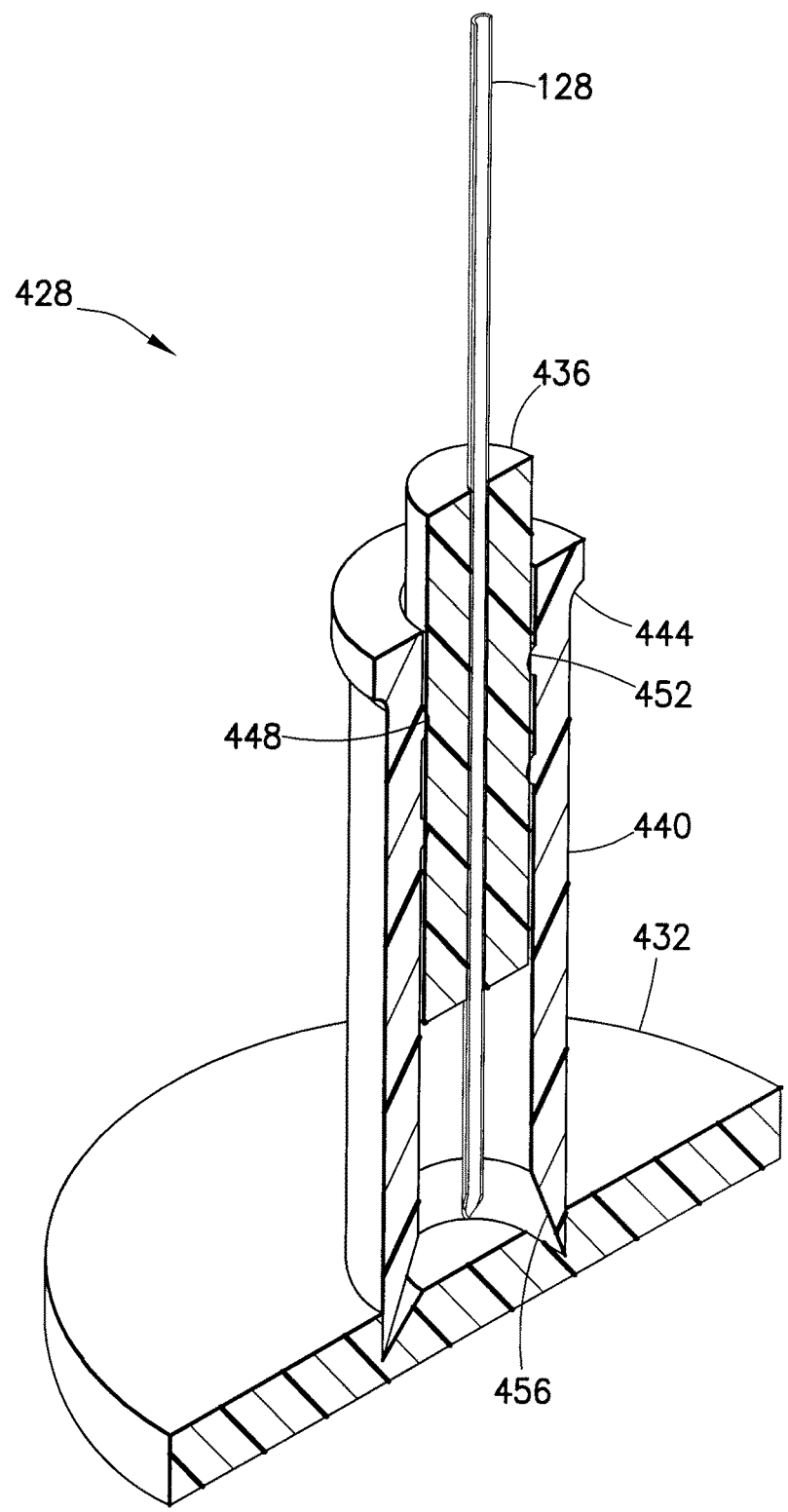
FIG. 50 is a perspective view in cross-section of a tenth alternative sterility barrier of the needle changing device of FIG. 3.

FIG. 50 is a partial perspective view in cross-section of a tenth alternative sterility barrier 428 for the changing device 100. For clarity, the patient end of only a single needle 128 is shown. The sterility barrier 428 includes a sterile floor 432 disposed at a distal end of the inner housing 108, the needle hub 436 disposed around a portion of the patient end of the needle 128, and introducer 440. According to one embodiment, sterile floor 432 is a septum 432. Alternatively, the sterile floor 432 the floor of a plastic housing, a thin, pierceable foil, or a trapped piece of foil or film. The introducer 440 has a shoulder 444 and at least one inwardly protruding circumferential protrusion 448 that selectively engages a circumferential depression 452 in the needle hub 436. Additionally, the introducer 440 has a beveled distal cutting tip or chisel 456. The introducer 440 may be made of, for example, metal or plastic.

Shown in mid-operation in FIG. 50, as the needle 128 is distally displaced, because of the frictional engagement between the circumferential protrusion 448 and the circumferential depression 452, the distal cutting tip 456 cuts through the portion of the sterile floor 432. Subsequent to this cutting, once the shoulder 444 engages the sterile floor 432 with the continued distal displacement of the needle 128, further distal displacement of the needle 128 results in the circumferential depression 452 disengaging with the circumferential protrusion 448, and needle hub 436 displacing distally relative to the introducer 440, thereby exposing the distal end of the needle 128 outside of the changing device 100. As the needle 128 is re-sheathed within the inner housing 108, the needle hub 436 and the introducer 440 maintain the relative positions that they possessed at the distal end of the needle's stroke.

According to one embodiment, the distal cutting tip 456 of the introducer 440 is disposed around the circumference of the distal end of the introducer 440. According to another embodiment, the distal cutting tip 456 is disposed only around a portion of the circumference (for example, 180° or 270°) of the distal end of the introducer 440. In such an embodiment, the introducer 440 cuts a flap that folds out of the way when the needle 128 is exposed outside of the device 100. Such an embodiment also prevents particulate (for example, a piece entirely cut out of the sterile floor 432) from falling out of the changing device 100.

Figure 51:
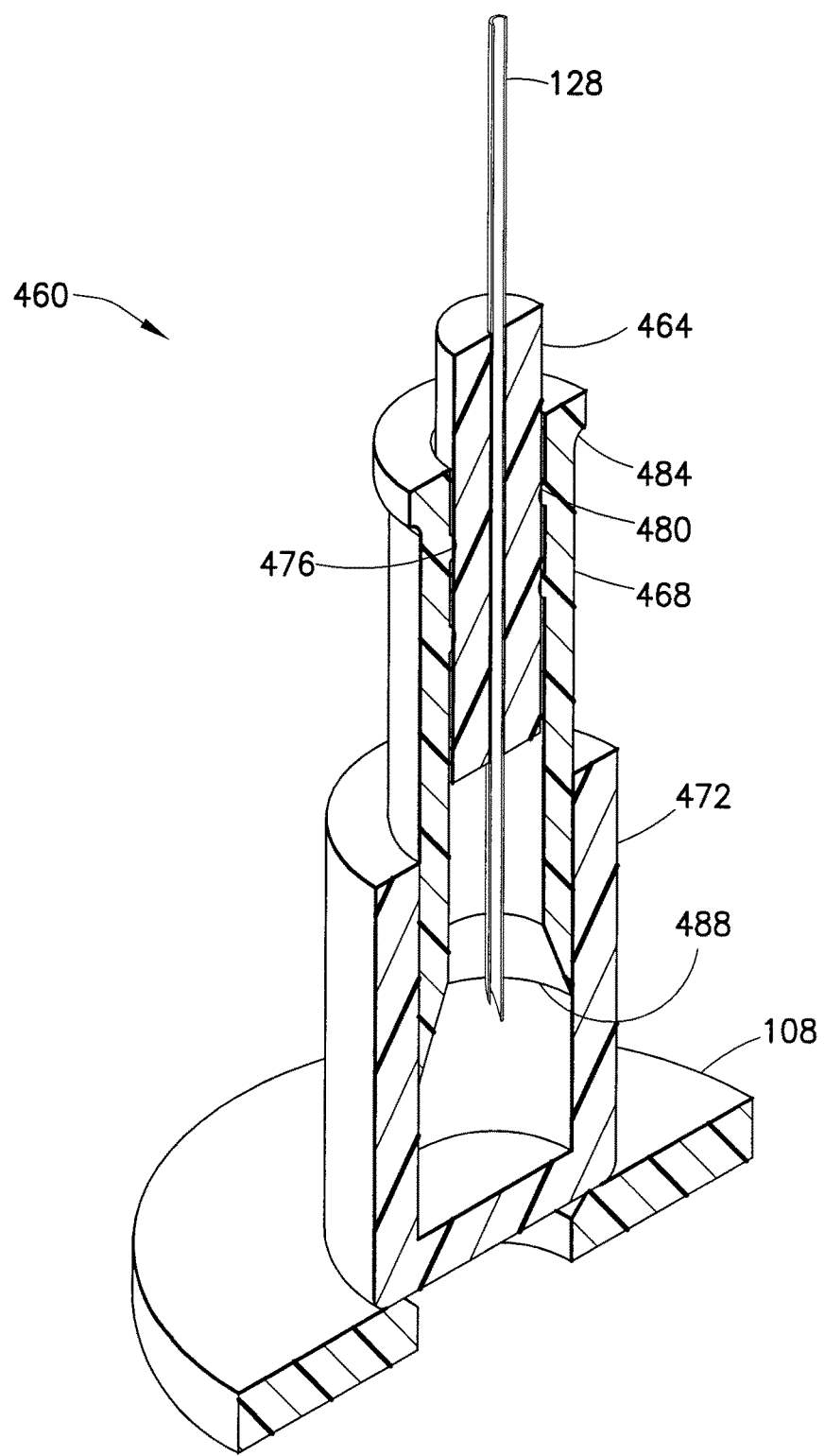
FIG. 51 is a perspective view in cross-section of an eleventh alternative sterility barrier of the needle changing device of FIG. 3.

FIG. 51 is a partial perspective view in cross-section of an eleventh alternative sterility barrier 460 for the changing device 100. For clarity, the patient end of only a single needle 128 is shown. The sterility barrier 460 includes a needle hub 464 disposed around a portion of the patient and of the needle 128, an introducer 468, and a boot 472. The needle hub 164 includes at least one circumferential depression selectively engaged with a corresponding circumferential protrusion 480 on the introducer 468. The introducer 468 also has a shoulder 484 and a beveled distal cutting tip or chisel 488.

As shown in FIG. 51, the floor of the inner housing 108 has an opening 492 therethrough corresponding to each of the plurality of needles 128. The openings 492 are radially spaced from a central axis of the inner housing 108.

Shown in mid-operation in FIG. 51, as the needle 128 is distally displaced, because of the frictional engagement between the circumferential protrusion 480 and the circumferential depression 476, as well as the frictional engagement between the introducer 468 and the boot 472, the sterility barrier 460 travels with needle 128 until the boot 472 contacts the floor of the inner housing 108.

With continued distal displacement of the needle 128, the friction between the boot 472 and the introducer 468 is overcome and the distal cutting tip 488 cuts the floor of the boot 472 and travels distally along with the needle 128 until the shoulder 484 contacts a proximal and of the boot 472. With further distal displacement of the needle 128, the friction between the circumferential depression 476 and the circumferential protrusion 480 is overcome and the distal end of the needle 128 is exposed outside of the changing device 100 through the opening in the boot 472 cut by the distal cutting tip 488 and through the opening 492 in the floor of the inner housing 108. As the needle 128 is re-sheathed within the inner housing 108, the needle hub 464, introducer 468, and the boot 472 maintain the relative positions that they possessed at the distal end of the needle's stroke.

Figure 52:
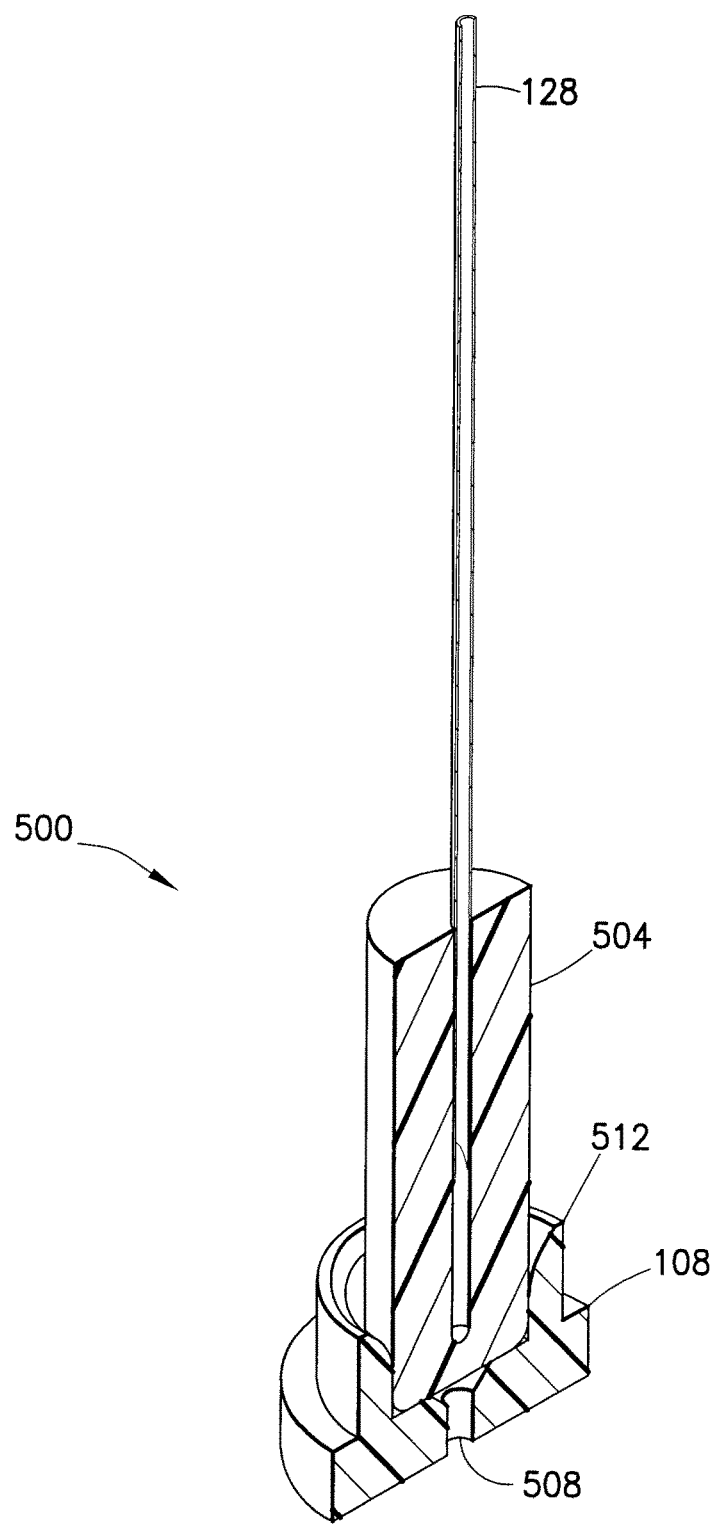
FIG. 52 is a perspective view in cross-section of a twelfth alternative sterility barrier of the needle changing device of FIG. 3.

FIG. 52 is a partial perspective view in cross-section of a twelfth alternative sterility barrier 500 for the changing device 100. For clarity, the patient end of only a single needle 128 is shown. The sterility barrier 500 includes a boot 504. As shown in FIG. 52, the floor of the inner housing 108 has an opening 508 therethrough corresponding to each of the plurality of needles 128. The openings 508 are radially spaced from the central axis of the inner housing 108.

Shown in mid-operation in FIG. 52, as the needle 128 is distally displaced, the boot 504 travels with needle 128 until the boot 504 contacts the floor of the inner housing 108. With further distal displacement, the needle 128 pierces the boot 500 and exposed outside of the changing device 100 through the opening 508. According to one embodiment, the floor of the inner housing 108 also includes a collar 512 with a beveled proximal edge for guiding the boot 504. As the needle 128 is re-sheathed within the inner housing 108, the boot 504 maintains the relative position that it possessed at the distal end of the needle's stroke.

Figure 53:
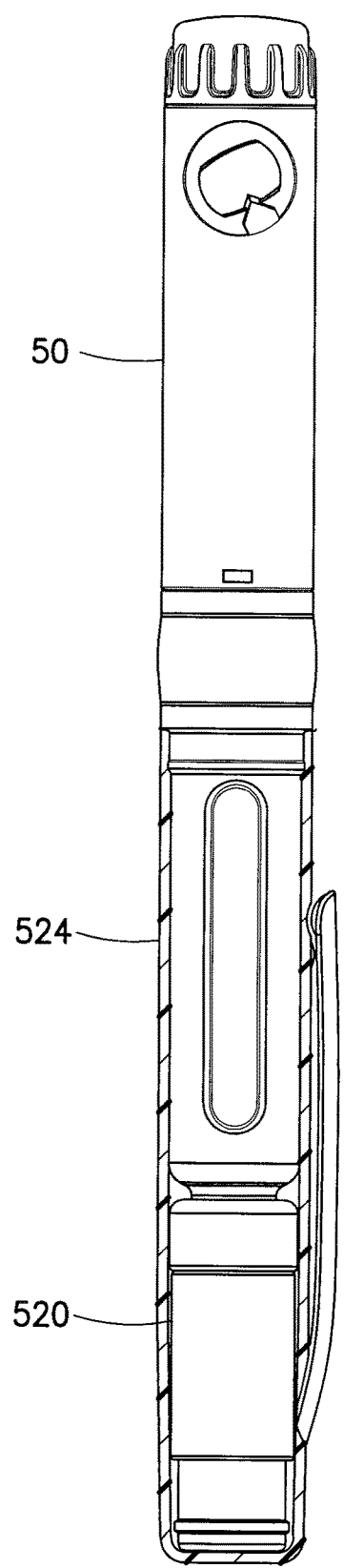
FIG. 53 is a perspective view of a pen injection device and a needle changing device according to another embodiment of the present invention.

FIG. 53 is a perspective view of the pen injector 50 and a needle changing device 520 (for brevity, hereinafter changing device 520) according to another embodiment of the present invention. Compared with the changing device 100, the changing device 520 has a smaller profile. For convenient storage, a cap 524 covers the changing device 520 while the changing device 520 is connected to the pen injector 50.

Figure 54:
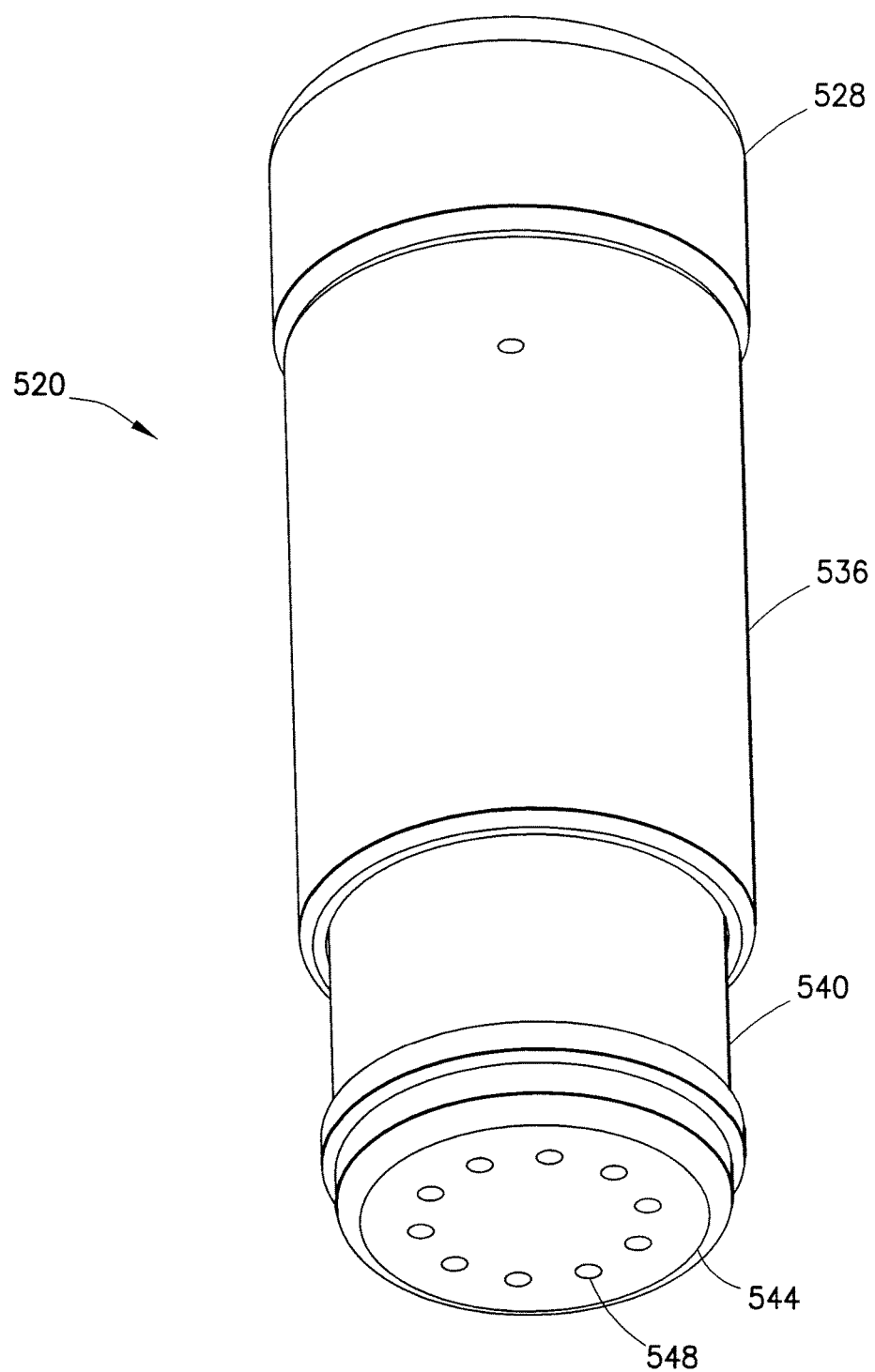
FIG. 54 is a perspective view of the needle changing device of FIG. 53.
Figure 55:
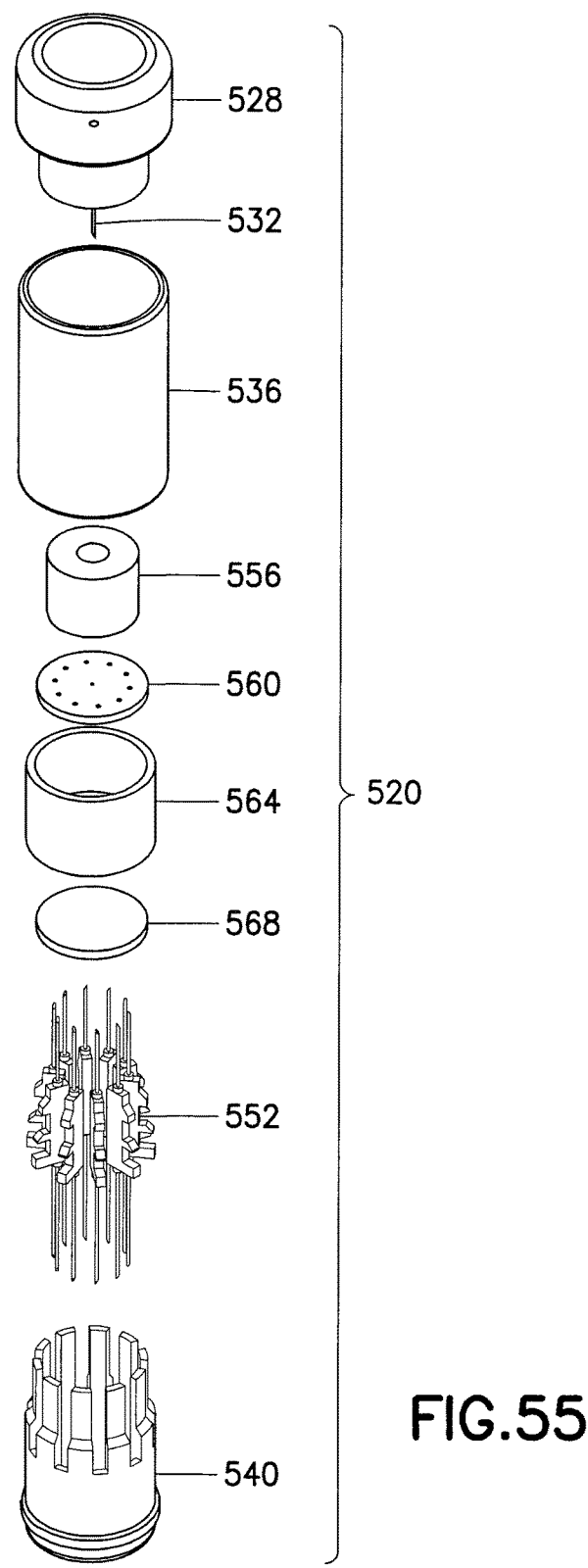
FIG. 55 is an exploded perspective view of the needle changing device of FIG. 53.
Figure 56:
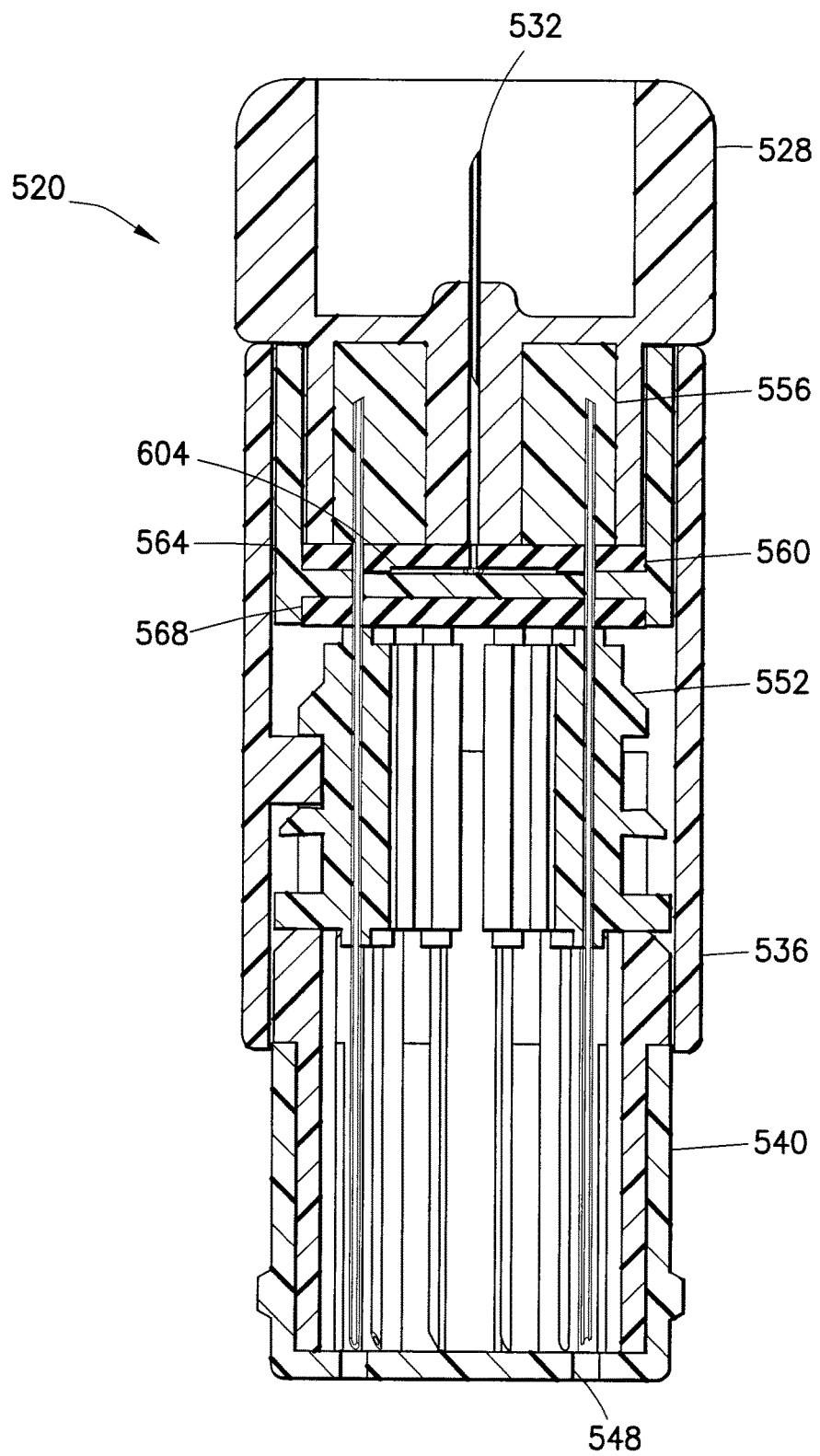
FIG. 56 is a perspective view in cross-section of the needle changing device of FIG. 53.

FIG. 54 is a perspective view of the changing device 520, FIG. 55 is an exploded perspective view of the changing device 520, and FIG. 56 is a perspective view in cross-section of the changing device 520. As shown in FIGS. 54, 55, and 56, the changing device 520 includes an adapter 524 connecting the changing device 520 with the pen injector 50, outer housing 536, and an inner housing 540. The outer housing 536 rotates and axially displaces relative to the inner housing 540. The bottom floor 544 of the inner housing 540 includes a plurality of openings 548 therethrough respectively corresponding to a plurality of needles 552 disposed within the inner housing 540.

Additionally, the changing device 520 includes an adapter cannula 532 connected with the adapter 528, a top septum 556, a channel disk 560, an adapter channel 564, and a reservoir septum 568. Other details of the changing device 520, such as the needle counter and needle selecting mechanisms, are omitted for brevity and clarity. Other than the noted exceptions described in greater detail below, the changing device 520 functions substantially similarly to the changing device 100 described above.

Figure 57:
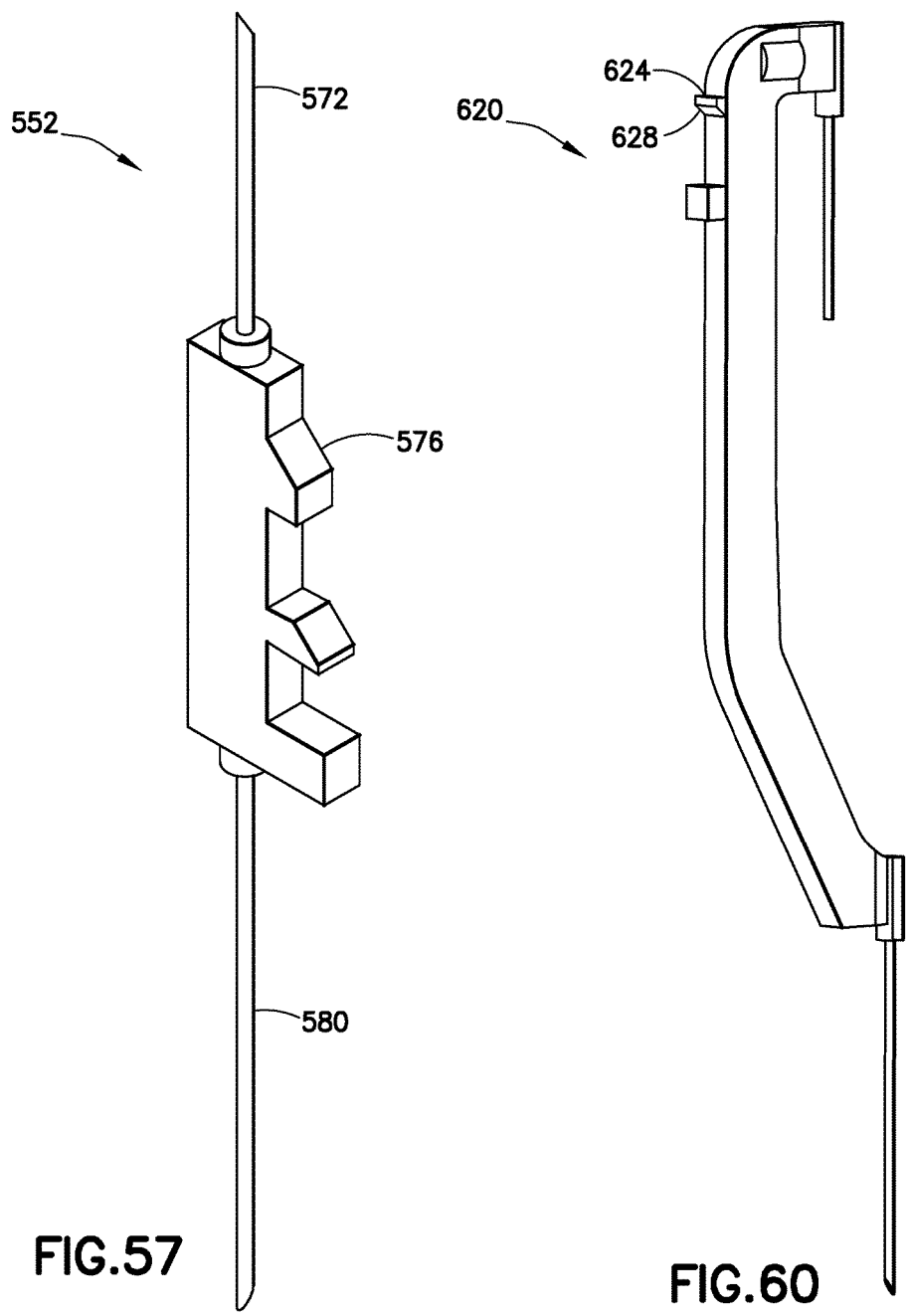
FIG. 57 is a perspective view of a needle of the needle changing device of FIG. 53.

FIG. 57 is a perspective view of needle 552 of the changing device 520. Most notably, in comparison with the needle 128, the needle 552 substantially straight. The needle 552 includes a septum portion 572 for piercing the reservoir septum 568 and communicating with reservoir, a hub or engaging portion 576 for interacting with the selecting mechanism, and a patient portion 580 in fluid communication with the septum portion 572, for piercing a patient's skin. According to one embodiment, the proximal end of the needle 552 is open for communication with a reservoir 604 described in greater detail below. According to another embodiment, the proximal end of the needle 552 is closed, and a side opening is disposed distally spaced from the proximal end of the needle 552 for communication with the reservoir 604.

Figure 58:
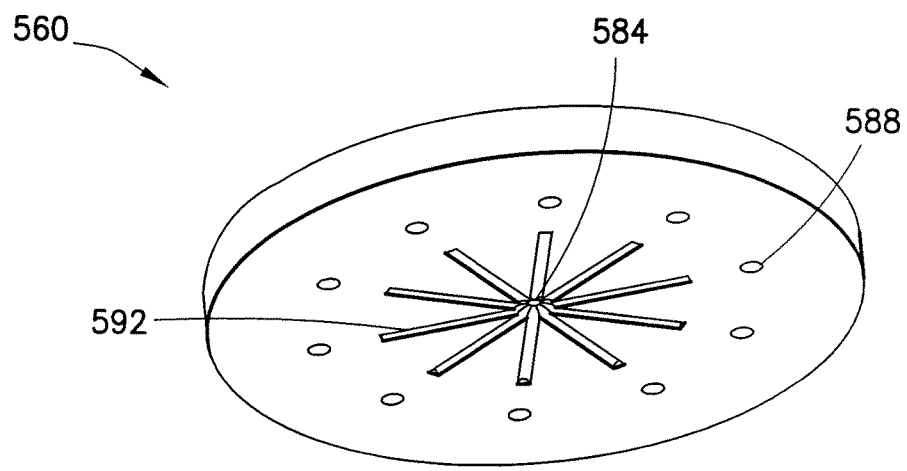
FIG. 58 is a perspective bottom view of a channel disk of the needle changing device of FIG. 53.

FIG. 58 is a perspective bottom view of the channel disk 560. As shown in FIG. 58, the channel disk 560 includes a central aperture 584 may communicates with the adapter cannula 532, which communicates with the medicament cartridge 12 of the pen injector 50. The channel disk 560 also includes a plurality of openings 588 therethrough respectively corresponding to the plurality of needles 552, and a plurality of radial channels 592 connected with the central aperture 504 and also respectively corresponding to the plurality of needles 552.

Figure 59:
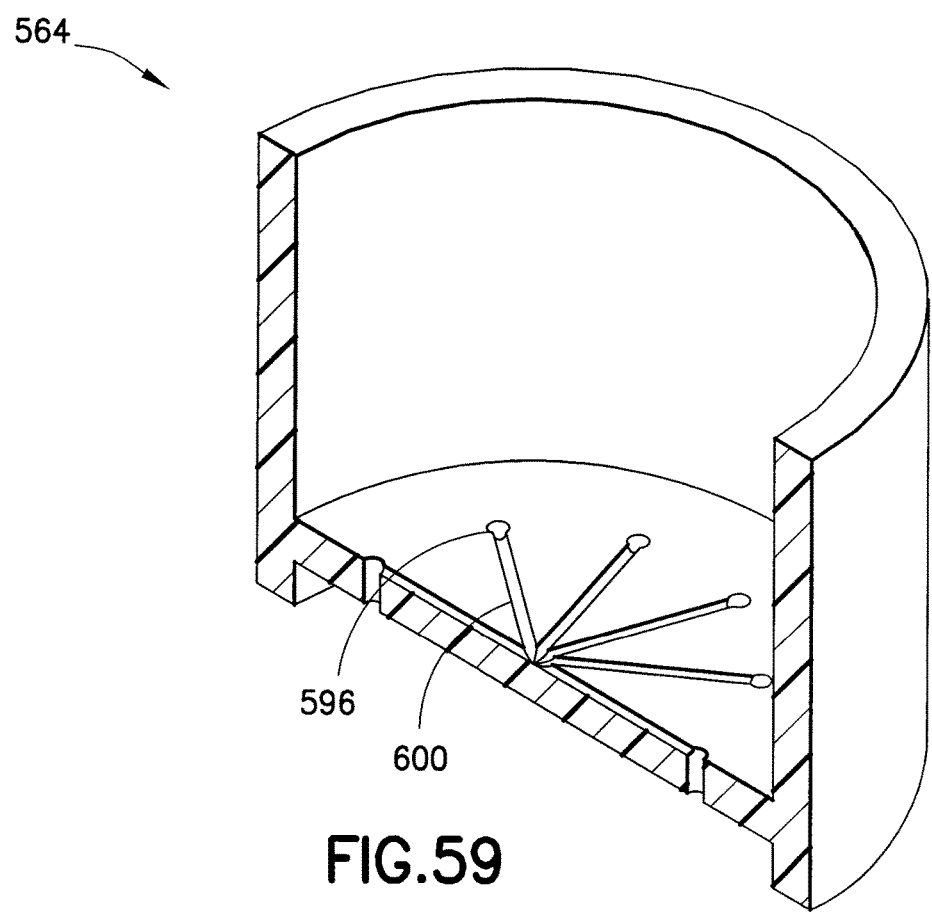
FIG. 59 is a top perspective view in cross-section of an adapter channel of the needle changing device of FIG. 53.

FIG. 59 is a top perspective view in cross-section of the adapter channel 564, which has a plurality of openings 596 through a floor thereof and the corresponding plurality of radial channels 600 fluidly communicating with the plurality of openings 596. The plurality of openings 596 and the plurality of radial channel 600 respectively correspond with the plurality of needles 552. Referring to FIGS. 58 and 59, together, the radial channels 592 and 600 cooperate to form a reservoir 604.

Referring back to FIGS. 55 and 56, prior to selection of a needle 552, the septum portions 572 of needles 552 pass through the septum 568, the openings 596 and the openings 588, such that the proximal ends of the septum portions 572 are disposed within the top septum 556, which provides a sterile barrier for the proximal ends of the septum portions 572. The previously-described sterility barriers serve as sterile barriers for the distal ends of the patient portions 580 of the plurality of needles 552.

Once the needle 552 is selected, distal displacement of the outer housing 536 distally displaces the selected needle 552. At the end of the distal stroke of the needle 552, the septum portion 572 of the selected needle (and thus, the patient portion 580) fluidly communicates with the reservoir 604, thereby permitting injection of the medicament from the medicament cartridge through the adapter cannula 532, the adapter 528, the reservoir 664, and the selected needle 552 into the patient. Subsequently, along with the proximal displacement of the outer housing 536, the selected needle 552 displaces proximally to re-sheath the patient portion 580 within the inner housing 540 and re-sheath the proximal end of the septum portion 572 within the top septum 556.

According to one embodiment, a given needle 200 or 552 is not reusable after a user has rotated the outer housing 104 or 536 to select the next needle. To accommodate emergency situations, however, it is helpful for a user to be able to access and reuse, for example, a final one of the plurality of needles. FIG. 60 illustrates a final needle 620 for use with the changing device 100 or the changing device 520. As shown in FIG. 60, the final needle 620 has a structure 624 for interacting with the needle selection mechanism to permit repeated access to the final needle 620. According to one embodiment, the structure 624 is an upper needle protrusion 624. Unlike the needle 200 shown in FIG. 6, however, the upper needle protrusion 624 of the final needle 620 has a chamfer 628 on a distal surface thereof. Accordingly, with such a chamfer 628, the beveled portion 300 of the protrusion 264, for example, can be displaced proximally relative to the final needle 620, so that the final needle 620 can again be selected for distal displacement and thus, re-use.

Although the previously-described embodiments refer to pen injection devices, it will be understood by one skilled in the art that embodiments of the present invention may also be used with other medicament injection devices, such as syringes.

Changing typical pen needle assemblies for pen injectors takes up to six user steps to install and remove from the pen; in addition, the user may be vulnerable to accidental needle-sticks when manipulating the pen needle assembly. Embodiments of the present invention provide novel means for changing needles in a contained, efficient, and user-friendly manner. An array of needles is contained within the changing device, attached to the end of a typical pen, or likewise, integrated into a specially designed delivery device. The changing device itself has an exterior twisting dial (e.g., outer housing 104) for the user to engage a new needle for use. The dial can then be pushed in the distal direction with respect to the pen injector. As the user pushes the dial or outer housing distally, the proximal end of the new needle pierces a septum adapter, opening a fluid path to the pen cartridge, and the distal end of the new needle is exposed for insertion into the delivery site. When the delivery is complete, the user simply pulls the dial proximally, sheathing the exposed needle. The user can now advance the dial to the next needle and start the process again.

In some embodiments of the present invention, the adapter changes the direction of the typical cartridge septum, which normally faces the distal end of a typical injection pen. This adapter clamps a ring shaped septum about the pen diameter while tapping the cartridge septum with an integrated needle. Between this ring-shaped septum, which faces proximally up the pen, and the cartridge tap, a small fluid cavity is created. The needles are hook-shaped, meaning the end used to pierce the ring shaped septum are bent 180° so that they extend in substantially the same direction as the distal end of the needle. This shape permits the needles to be stored circumfrentially about the pen. According to one embodiment, prior to selection, the needles are all partially inserted into the reversed septum. According to another embodiment, prior to selection, none of the needles are inserted into the reversed septum, but each needle is ready to be inserted into the reversed septum upon selection thereof. This partial insertion acts as a sterility barrier, as well as a means of solidly fixing the needles in the device. As the radial dial turns, the radial dial's selector feature engages individual needles. By moving the dial vertically down the pen, the hook-shaped needle pierces the reversed septum and exposes itself through another septum integrated in the distal end of the device. Needles are sheathed, and returned to their nominal storage state by pulling back on the dial or outer housing.

Currently there are no fully automatic needle changing devices on the market. There are many examples of devices that aid with individual steps of the needle changing process, including needle storage, needle attachment, needle removal, and needle disposal, but none of these devices integrate the needle changing processes into one device.

By storing the needles around the circumference of the pen, a user can avoid carrying bulky injection "kits". With an integrated device, all needles can be stored with the pen. In addition, according to one embodiment, the device stores new needles in a sterile manner, storing needles within septa that act as sterility barriers. This allows storage of used needles alongside the new ones. Therefore, the device can also function as a used sharps container.

Cumbersome and potentially dangerous needle attachment is made easier for the user. The interfaces of embodiments of the present invention are more user friendly than the typical pen needle hub. With this invention, the user interfaces with a dial, advancing to new needles with a twist, and piercing the septum with an upward pull on the pen injector (which is a push downward on the outer housing or dial). With current needles used for pen injectors, the user must remove the top of the needle container, twist the needle onto the pen, remove the needle container, and then finally remove a needle cap. While there are some needle storage devices that aid in placing the needle hub on the pen, the user still must remove needle hub packaging, including the inner needle sheath, to place a needle hub onto a typical pen injector and ready it for injection. With embodiments of the current invention, the typical four meticulous steps with small sharp needle hubs can be reduced to three intuitive steps with ergonomic user interfaces.

Needle removal and disposal can also be simplified with embodiments of the present invention. There are many devices that aid in removing needles from pens after use, including needle clipping devices and sharps containers that pull the needle from the pen body. But these devices are more cumbersome to use than embodiments of the present invention. With embodiments of the present invention, the user can simply slide a dial proximally up relative to the pen, automatically re-sheathing the exposed needle.

Embodiments of the present invention can integrate the needle changing process into a single device. Needle storage, needle attachment, needle removal, and needle disposal can now be accomplished via a single system. In some embodiments, hook-shaped needles are located around the perimeter of the device, inserted into a reversed septum. In other embodiments, straight needles are similarly arrayed around the perimeter of the device. When the user turns the external dial, a vertical movement feature is moved to a new needle. As the user pushes distally on this dial, the selected needle pierces the reservoir septum, opening a fluid path. In addition, the needles can be embedded in a distal septum (sterility barrier). The selected needle pierces through the distal septum, exposing itself for injection. The needle is pulled back into the device when the user pulls upward on the dial.

According to one embodiment, the manual needle retraction can be made automatic by having a needle shield (not shown) incorporated into the device as a means of sensing medication delivery. According to another embodiment, the needle shield can act as a safety and prevent fluid flow from the distal end of the needle until the shield is compressed back into the device. According to yet another embodiment (not shown), compressing the needle shield back into the device can trigger a spring return, which automatically retracts the needle into the device.

In embodiments of the present invention, the overall needle assembly can be made from a plastic tube with metal needles attached to both ends and features to activate the needles to pierce the septa. In contrast, in an embodiment in which a straight metal needle is bent to the desired shape, at the point of the bend, and when the bend radii are small, the inner diameter of the needle can be slightly reduced. This narrowing of the inner diameter can result in a rise of injection pressure. The bend radii of the exemplary embodiments of the present invention, however, are likely large enough to minimize such an injection pressure rise. As an alternative, a larger inner diameter metal needle may be employed to achieve the desired inner diameter subsequent to bending, but this portion may increase the expense of manufacturing the device and may result in an outer needle diameter undesirable for the patient. Nevertheless, in an embodiment with a plastic tube and metal needles, high injection pressures can be prevented, the desired outer needle diameter needle implemented, and the needle assembly manufactured more simply.

In an exemplary embodiment of the present invention, each new needle (i.e., prior to being used for an injection) stored in the needle changing device is individually sterile, thereby preventing contamination of a new needle by a used needle. For example, a sterility barrier is provided for each new needle.

In another exemplary embodiment of the present invention, each used needle remains accessible such that the user has access to the used needles in case of an emergency. Alternatively, of the used needles, only the last-used needle is always accessible, thereby providing an available needle in case of emergency.

Although only a few embodiments of the present invention have been shown and described, the present invention is not limited to the described embodiments. Instead, it will be appreciated by those skilled in the art that changes may be made to these embodiments without departing from the principles and spirit of the invention, the scope of which is defined by the appended claims and their equivalents.

What is claimed is:

1. An apparatus for storing and changing needles for connection with a medicament delivery device, the apparatus comprising:
    a housing having a floor disposed at a distal end thereof;
    a needle holder disposed within the housing, for fluidly connecting with a medicament container of the medicament delivery device;
    a plurality of needles displaceably disposed on the needle holder;
    a user interface disposed on the housing to individually select one of the plurality of needles and displace the selected needle; and
    a plurality of sterility barriers for ensuring sterility of a patient portion of each needle prior to exposure to an outside of the apparatus;
    wherein each sterility barrier comprises:
        a needle hub disposed around a portion of the patient portion of the needle; and
        an introducer, adapted to slide relative to the needle hub, the introducer having a distal cutting tip adapted to cut an opening to access the outside of the apparatus through the floor.

2. The apparatus according to claim 1, wherein:
the floor is sterile;
the introducer is adapted to cut the opening in the sterile floor;
the introducer has a proximal shoulder adapted to engage the sterile floor subsequent to cutting the sterile floor; and
the sterility barrier is adapted such that subsequent to engagement between the proximal shoulder and the sterile floor, further distal displacement of the needle distally displaces the needle hub relative to the introducer and exposes an end of the patient portion to the outside of the apparatus.

3. The apparatus according to claim 1, wherein:
each sterility barrier further comprises a boot adapted to slide relative to the introducer, the boot having a sterile floor at a distal end thereof;
the introducer has a proximal shoulder adapted to engage the sterile floor of the boot;
wherein the sterility barrier is adapted such that during distal displacement of the needle, subsequent to contact between the boot and the floor of the housing, the introducer distally displaces relative to the boot and cuts the opening in the sterile floor of the boot; and
wherein the sterility barrier is adapted such that subsequent to engagement between the proximal shoulder and the sterile floor of the boot, further distal displacement of the needle distally displaces the needle hub relative to the introducer and exposes an end of the patient portion to the outside of the apparatus.

4. A combination, comprising:
a medicament delivery device having a medicament container; and
an apparatus for storing and changing needles, the apparatus being connectable with the medicament delivery device, the apparatus comprising:
    a housing having a floor disposed at a distal end thereof, and a having a reservoir disposed therein, the reservoir being fluidly connected with the medicament container when the apparatus is connected with the medicament delivery device;
    a needle holder disposed within the housing, for fluidly connecting with the medicament container of the medicament delivery device;
    a plurality of needles displaceably disposed on the needle holder;
    a user interface disposed on the housing to individually select one of the plurality of needles and displace the selected needle; and
    a plurality of sterility barriers for ensuring sterility of a patient portion of each needle prior to exposure to an outside of the apparatus;
    wherein each sterility barrier comprises a boot disposed at a distal end of the patient portion of the needle.

5. The apparatus according to claim 4, wherein the sterility barrier is adapted such that during distal displacement of the needle, subsequent to contact between the boot and the floor of the housing, the needle pierces a distal end of the boot and passes through an opening in the floor of the housing, exposing an end of the patient portion to the outside of the apparatus.

6. An apparatus for storing and changing needles for connection with a medicament delivery device, the apparatus comprising:
    a housing having a floor disposed at a distal end thereof;
    a needle holder disposed within the housing, for fluidly connecting with a medicament container of the medicament delivery device;
    a plurality of needles displaceably disposed on the needle holder;
    a user interface disposed on the housing to individually select one of the plurality of needles and displace the selected needle; and a plurality of sterility barriers for ensuring sterility of a patient portion of each needle prior to exposure to an outside of the apparatus;

wherein each sterility barrier comprises:
- a boot disposed at a distal end of the patient portion of the needle;
- a needle hub disposed around a portion of the patient portion of the needle; and
- an introducer, slidable relative to the needle hub;

wherein the boot is adapted to slide relative to the introducer, the boot having a sterile floor at a distal end thereof;

wherein the introducer has a distal cutting tip adapted to cut a portion of the sterile floor, and a proximal shoulder adapted to engage the boot;

wherein each sterility barrier is adapted such that during distal displacement of the needle, subsequent to contact between the boot and the floor of the housing, the introducer distally displaces relative to the boot and cuts the sterile floor; and wherein each sterility barrier is adapted such that subsequent to engagement between the proximal shoulder and the boot, further distal displacement of the needle distally displaces the needle hub relative to the introducer and exposes an end of the patient portion to the outside of the apparatus.

\* \* \* \* \*